(12) United States Patent
Sumida et al.

(10) Patent No.: US 11,505,456 B2
(45) Date of Patent: Nov. 22, 2022

(54) METHOD FOR PRODUCING HOLLOW STRUCTURE AND HOLLOW STRUCTURE

(71) Applicant: CANON KABUSHIKI KAISHA, Tokyo (JP)

(72) Inventors: Takayuki Sumida, Kawasaki (JP); Ayako Maruyama, Kawasaki (JP); Takahiro Akiyama, Atsugi (JP); Yutaka Setomoto, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 520 days.

(21) Appl. No.: 16/723,686

(22) Filed: Dec. 20, 2019

(65) Prior Publication Data

US 2020/0123005 A1  Apr. 23, 2020

Related U.S. Application Data

(63) Continuation of application No. PCT/JP2018/023948, filed on Jun. 25, 2018.

(30) Foreign Application Priority Data

Jun. 30, 2017  (JP) .............................. JP2017-129351

(51) Int. Cl.
*B81C 1/00* (2006.01)
*B06B 1/02* (2006.01)
(Continued)

(52) U.S. Cl.
CPC ........ *B81C 1/00531* (2013.01); *B06B 1/0292* (2013.01); *B81B 3/0021* (2013.01);
(Continued)

(58) Field of Classification Search
CPC ............ B81C 1/00531; B81C 1/00158; B81C 1/00476; B81C 1/00047; B06B 1/0292;
(Continued)

(56) References Cited

U.S. PATENT DOCUMENTS

2009/0301200 A1* 12/2009 Tanaka ................. B06B 1/0292
 73/603
2010/0207485 A1* 8/2010 Dirksen ............... B06B 1/0292
 310/300

(Continued)

FOREIGN PATENT DOCUMENTS

JP 2008-288813 A 11/2008
JP 2013-506284 A 2/2013
(Continued)

*Primary Examiner* — Alexander Krzystan
*Assistant Examiner* — Julie X Dang
(74) *Attorney, Agent, or Firm* — Canon U.S.A., Inc., IP Division

(57) ABSTRACT

A method includes a step of forming a sacrificial layer on a first film, a step of forming a second film on the sacrificial layer, a step of forming an etching opening that extends through at least one of the first film and the second film so as to communicate with the sacrificial layer, and a step of forming a hollow portion by etching the sacrificial layer using a gas containing a fluorine-containing gas and hydrogen via the etching opening, wherein a composition ratio of silicon to nitrogen in a first region having a face in contact with the sacrificial layer is larger than a composition ratio of silicon to nitrogen in a second region not including the first region.

12 Claims, 25 Drawing Sheets

(51) Int. Cl.
    *H04R 19/00*      (2006.01)
    *B81B 3/00*       (2006.01)
(52) U.S. Cl.
    CPC ....... *B81C 1/00158* (2013.01); *H04R 19/005* (2013.01); *B81C 1/00476* (2013.01)
(58) Field of Classification Search
    CPC .... B81B 3/0021; H04R 19/005; H04R 19/00; H04R 31/00; A61B 8/14; H01L 21/302
    See application file for complete search history.

(56) References Cited

U.S. PATENT DOCUMENTS

| | | | |
|---|---|---|---|
| 2011/0163630 A1* | 7/2011 | Klootwijk | B06B 1/0292 310/300 |
| 2012/0112603 A1* | 5/2012 | Masaki | B06B 1/0292 257/E21.219 |
| 2012/0256520 A1* | 10/2012 | Torashima | H01L 41/0973 29/25.35 |

FOREIGN PATENT DOCUMENTS

| | | |
|---|---|---|
| JP | 2013-145802 A | 7/2013 |
| JP | 2015-115631 A | 6/2015 |
| WO | 2013/005486 A1 | 1/2013 |

* cited by examiner

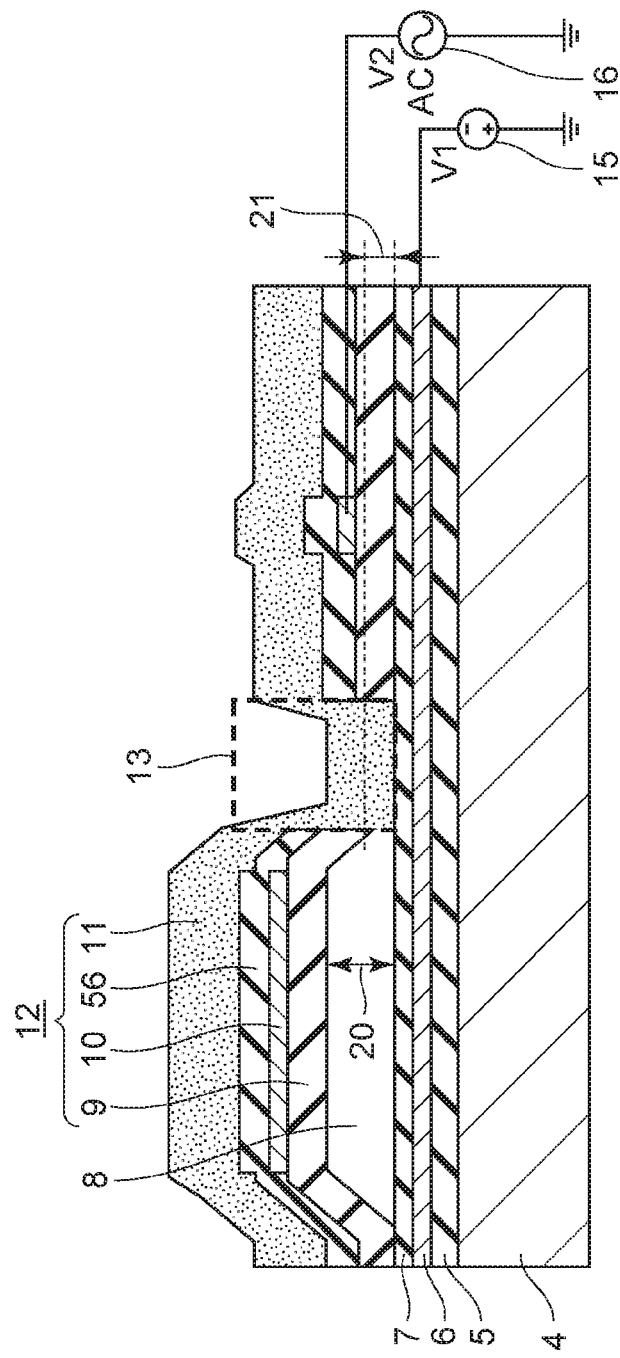

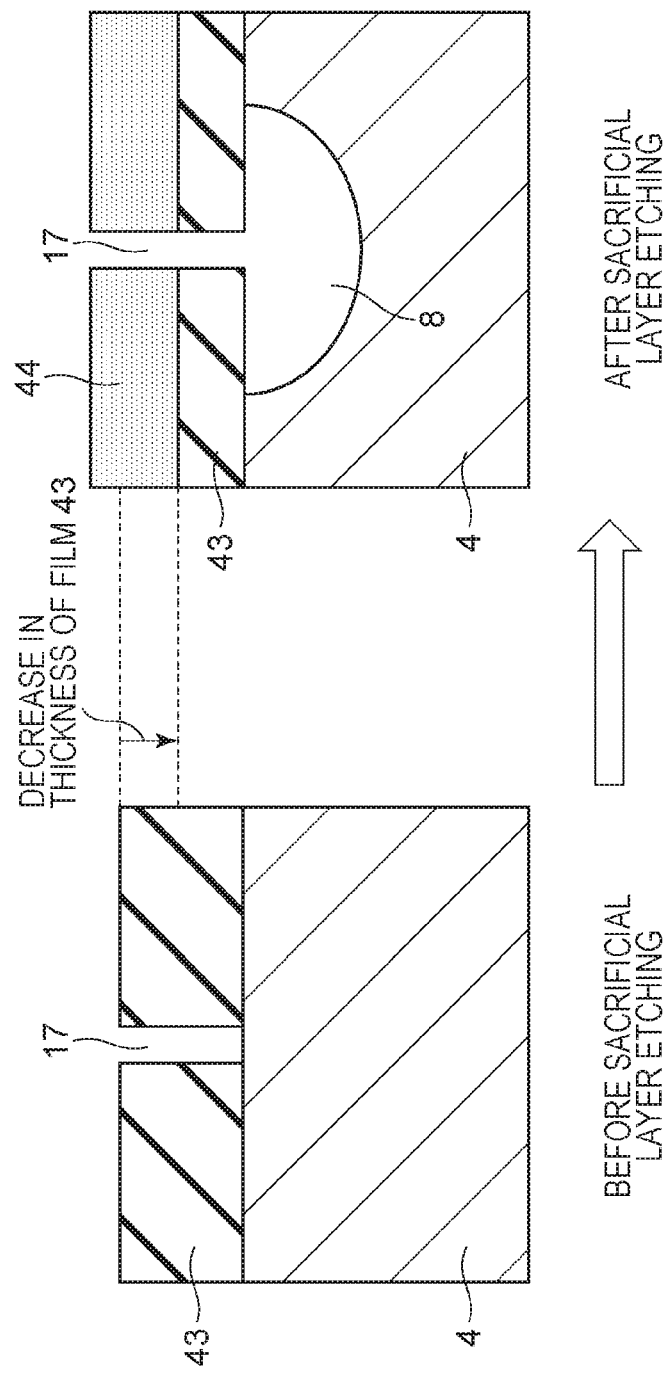

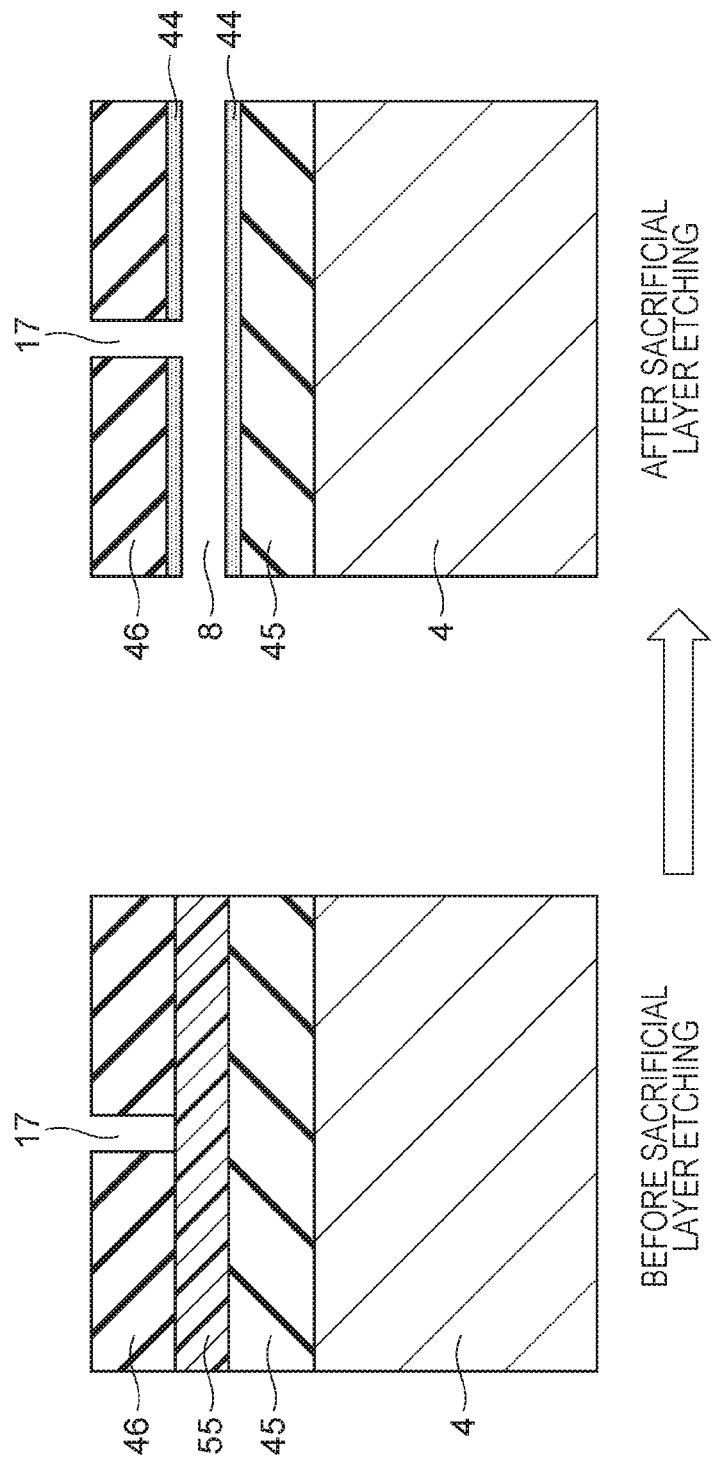

METHOD FOR PRODUCING HOLLOW STRUCTURE AND HOLLOW STRUCTURE

CROSS-REFERENCE TO RELATED APPLICATIONS

This application is a Continuation of International Patent Application No. PCT/JP2018/023948, filed Jun. 25, 2018, which claims the benefit of Japanese Patent Application No. 2017-129351, filed Jun. 30, 2017, both of which are hereby incorporated by reference herein in their entirety.

TECHNICAL FIELD

The present invention relates to a method for producing a hollow structure used as a capacitive transducer or the like and a hollow structure.

BACKGROUND ART

Capacitive transducers produced by micromachining technology have been studied as an alternative of piezoelectric devices. Hereafter, capacitive transducers may also be referred to as capacitive micromachined ultrasonic transducers (CMUTs). CMUTs generally include a hollow portion and a vibration film and are capable of transmitting and receiving acoustic waves (ultrasonic waves) using vibration of the vibration film, and good wide-band characteristics are achieved particularly in a liquid. One of methods for producing a CMUT is a method in which films are formed by stacking materials on a substrate such as a silicon substrate. Japanese Patent Laid-Open No. 2008-288813 (PTL 1) discloses that an insulating film, a silicon film serving as a sacrificial layer, and a vibration film are stacked on a substrate in this order, and the sacrificial layer is etched via an etching opening partly formed in the vibration film to form a hollow portion. Although xenon difluoride is used to remove the sacrificial layer, a sufficient etching selectivity is achieved between the sacrificial layer and the insulating film or the vibration film by using silicon oxide films as the insulating film and the vibration film that are in contact with the sacrificial layer. This suppresses etching of the insulating film and the vibration film.

From the viewpoint of improving the transmission and reception sensitivity of acoustic waves, silicon nitride films having a higher relative dielectric constant than silicon oxide films can be used as the insulating film and the vibration film.

However, when a silicon film is used as the sacrificial layer and silicon nitride films are used as the insulating film and the vibration film that are in contact with the sacrificial layer, a sufficient selectivity is not achieved during etching of the sacrificial layer with xenon difluoride. Consequently, the silicon nitride films may also be etched.

CITATION LIST

Patent Literature

PTL 1: Japanese Patent Laid-Open No. 2008-288813
PTL 2: PCT Japanese Translation Patent Publication No. 2013-506284

PCT Japanese Translation Patent Publication No. 2013-506284 (PTL 2) discloses a method in which an etching gas containing xenon difluoride and hydrogen is used to improve the etching selectivity between a silicon film and a silicon nitride film.

However, the present inventors have found that deposits grow during etching of the sacrificial layer with an etching gas containing xenon difluoride and hydrogen. The growth of deposits facilitates the blocking of an etching opening and a hollow portion. This poses a problem in that the etching gas cannot be supplied to the sacrificial layer to cause etching failure such as delay or stop of etching.

SUMMARY OF INVENTION

A method for producing a hollow structure according to an aspect of the present invention is a method for producing a hollow structure including a first film and a second film disposed so as to face the first film with a hollow portion formed therebetween, the method including a step of forming a sacrificial layer on a first film; a step of forming a second film on the sacrificial layer; a step of forming an etching opening that extends through at least one of the first film and the second film so as to communicate with the sacrificial layer; and a step of forming a hollow portion by etching the sacrificial layer using a gas containing a fluorine-containing gas and hydrogen via the etching opening, wherein at least one of the first film and the second film in which the etching opening is formed includes a silicon nitride film, and in the silicon nitride film, a composition ratio of silicon to nitrogen in a first region having a face in contact with the sacrificial layer is larger than a composition ratio of silicon to nitrogen in a second region not including the first region.

A method for producing a capacitive transducer according to an aspect of the present invention includes a step of forming a first film on a first electrode; a step of forming a sacrificial layer on the first film; a step of forming a second film on the sacrificial layer; a step of forming a second electrode on the second film; a step of forming an etching opening that extends through the second film so as to communicate with the sacrificial layer; and a step of forming a hollow portion by etching the sacrificial layer using a gas containing a fluorine-containing gas and hydrogen via the etching opening, wherein the second film includes a silicon nitride film, and in the silicon nitride film, a composition ratio of silicon to nitrogen in a first region having a face in contact with the sacrificial layer is larger than a composition ratio of silicon to nitrogen in a second region not including the first region.

A hollow structure according to an aspect of the present invention is a hollow structure including a first film and a second film disposed so as to face the first film with a hollow portion formed therebetween, wherein at least one of the first film and the second film includes a silicon nitride film, and in the silicon nitride film, a composition ratio of silicon to nitrogen in a first region having a face in contact with the hollow portion is larger than a composition ratio of silicon to nitrogen in a second region not including the first region.

A capacitive transducer according to an aspect of the present invention is a capacitive transducer including a first electrode; a first film disposed on the first electrode; a second film disposed so as to face the first film with a hollow portion formed therebetween; and a second electrode disposed on the second film, wherein at least one of the first film and the second film includes a silicon nitride film, and in the silicon nitride film, a composition ratio of silicon to nitrogen in a first region having a face in contact with the hollow portion is larger than a composition ratio of silicon to nitrogen in a second region not including the first region.

Further features of the present invention will become apparent from the following description of exemplary embodiments with reference to the attached drawings.

BRIEF DESCRIPTION OF DRAWINGS

FIG. 19 is a sectional view taken along line A-B in FIG. 1 in which a fourth insulating film is disposed in the CMUT according to an embodiment of the present invention.

FIG. 22 is a schematic sectional view of a structure for evaluating the characteristics of a silicon nitride film before and after sacrificial layer etching.

FIG. 23 is a schematic sectional view of a hollow structure before and after sacrificial layer etching.

DESCRIPTION OF EMBODIMENTS

Method for Producing Hollow Structure

Figure 1:
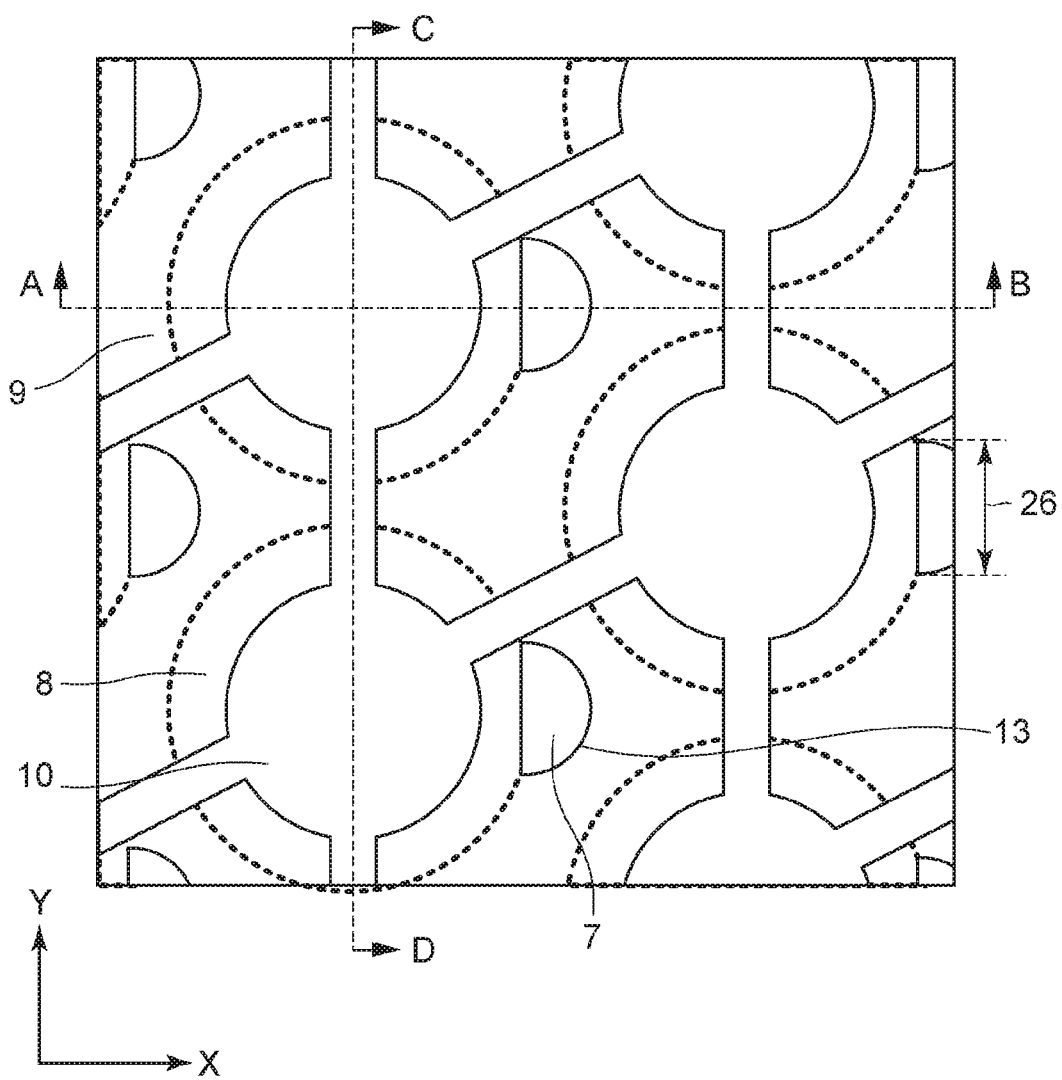
FIG. 1 is a top view for describing a CMUT according to an embodiment of the present invention.

A hollow structure according to an embodiment of the present invention will be described with reference to FIG. 24, but the present invention is not limited thereto.

A hollow structure 100 according to this embodiment includes a first film 101 and a second film 103 disposed so as to face the first film 101 with a hollow portion 102 formed therebetween. A method for producing the hollow structure 100 includes at least the following steps:

(1) a step of forming a sacrificial layer on a first film 101 (at a position indicated by the reference numeral 102), (2) a step of forming a second film 103 on the sacrificial layer, (3) a step of forming an etching opening 104 that extends through at least one of the first film 101 and the second film 103 so as to communicate with the sacrificial layer, and (4) a step of forming a hollow portion 102 by etching the sacrificial layer using a gas containing a fluorine-containing gas and hydrogen via the etching opening 104.

At least one of the first film 101 and the second film 103 in which the etching opening 104 is formed (the second film 103 in FIG. 24) includes a silicon nitride film (103). The silicon nitride film (103) has a first region 105 having a face in contact with the sacrificial layer and a second region 106 not including the first region 105. The composition ratio of silicon to nitrogen in the first region 105 is larger than the composition ratio of silicon to nitrogen in the second region 106. Hereafter, when the two regions are compared with each other, a relatively large composition ratio of silicon to nitrogen may be referred to as "silicon-rich (Si-rich)". Similarly, when the two regions are compared with each other, a relatively large composition ratio of nitrogen to silicon may be referred to as "nitrogen-rich (N-rich)". The composition ratio of nitrogen and silicon can be calculated by time-of-flight secondary ion mass spectrometry (TOF-SIMS).

When the silicon nitride film has a silicon-rich region that is in contact with the sacrificial layer, deposits are not easily formed even if a gas containing a fluorine-containing gas and hydrogen is used, which makes it difficult to cause etching failure. The refractive index of the silicon nitride film at a wavelength of 633 nm may be 1.90 or more because such deposits are not easily formed as described later.

The first film 101 can be formed on a substrate 110. When the substrate 110 is a silicon substrate, the production method may include a step of forming a thermally oxidized film by oxidizing the substrate 110.

In this embodiment, the fluorine-containing gas contains at least one selected from the group consisting of xenon difluoride, bromine trifluoride, chlorine trifluoride, and a fluorine-containing interhalogen compound. The fluorine-containing gas may be xenon difluoride.

Figure 24:
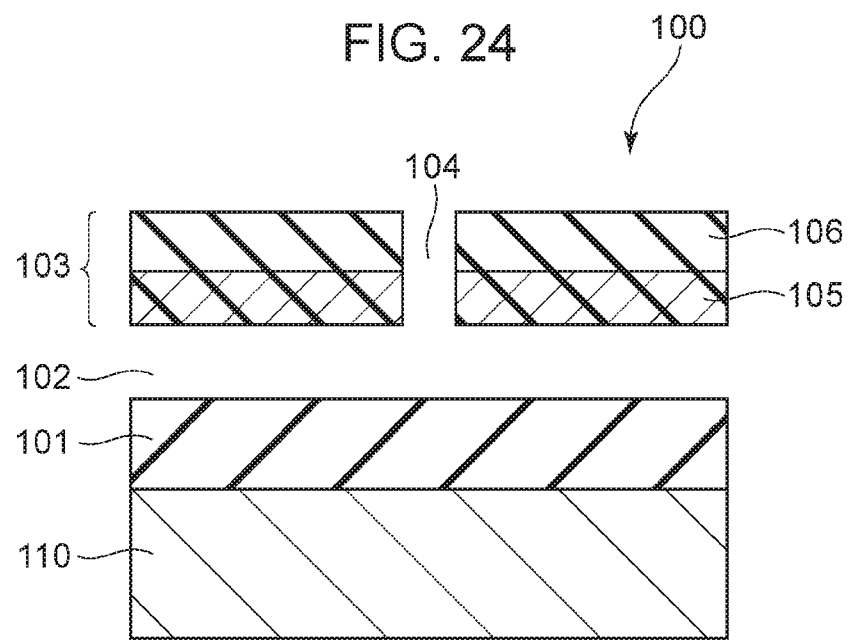
FIG. 24 is a diagram for describing a hollow structure and a method for producing the hollow structure according to an embodiment of the present invention.

FIG. 24 illustrates a two-layer structure including the first region 105 having a relatively high silicon content and the second region 106 having a relatively low silicon content, but the structure is not limited thereto. For example, the silicon nitride film may have a structure in which the ratio of silicon to nitrogen continuously decreases from one main surface at which the silicon nitride film is in contact with the sacrificial layer toward the other main surface. Obviously, the silicon concentration in the silicon nitride film may monotonously decrease, may decrease stepwise, or may decrease in a curved manner in a direction in which the films are stacked.

The silicon nitride film may have a structure in which the composition ratio of silicon to nitrogen in a third region having a face opposite to the face in contact with the sacrificial layer is larger than the composition ratio of silicon to nitrogen in the second region.

In the silicon nitride film, the composition ratio of nitrogen to silicon in the first region having a face in contact with the sacrificial layer may be smaller than the composition ratio of nitrogen to silicon in the second region.

It is difficult to completely eliminate deposits on the silicon nitride film even through the process in this embodiment. However, the deposits can be sublimated by heating the hollow portion under reduced pressure (e.g., 150 Pa or less).

Hollow Structure

The hollow structure 100 according to this embodiment will be described with reference to FIG. 24. The hollow structure 100 according to this embodiment includes a first film 101 and a second film 103 disposed so as to face the first film 101 with a hollow portion 102 formed therebetween. At least one of the first film 101 and the second film 103 includes a silicon nitride film. In FIG. 24, the second film 103 includes a silicon nitride film. In the silicon nitride film (103), the composition ratio of silicon to nitrogen in a first region 105 having a face in contact with the hollow portion 102 is larger than the composition ratio of silicon to nitrogen in a second region 106 not including the first region 105.

The refractive index of the silicon nitride film at a wavelength of 633 nm may be 1.90 or more.

The relative dielectric constant is higher in a structure in which the silicon nitride film is partly nitrogen-rich than in a structure in which the entire silicon nitride film is silicon-rich. This increases the transmission and reception sensitivity of ultrasonic waves in use of ultrasonic sensors such as CMUTs described later.

The hollow structure according to this embodiment can be used for piezoelectric devices such as ink jet devices and micropumps, microspeakers, fluid devices used for genetic diagnosis, and IR sensors such as bolometers.

Method for Producing CMUT

Figure 25:
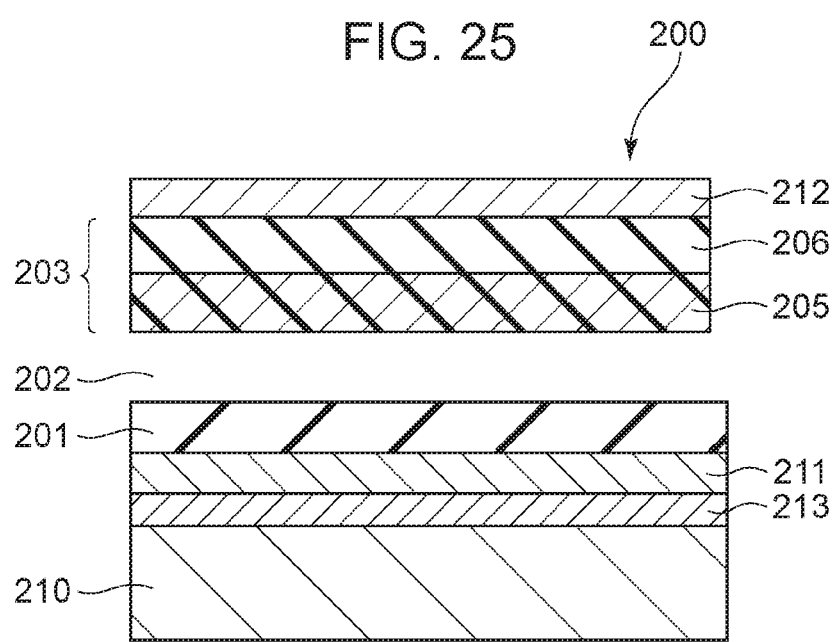
FIG. 25 is a diagram for describing a CMUT and a method for producing the CMUT according to an embodiment of the present invention.

The case where the hollow structure is a CMUT will be described with reference to FIG. 25. The method for producing a CMUT 200 according to this embodiment includes at least the following steps:

(1) a step of forming a first film 201 on a first electrode 211, (2) a step of forming a sacrificial layer on the first film 201 (at a position indicated by the reference numeral 202), (3) a step of forming a second film 203 on the sacrificial layer (202), (4) a step of forming a second electrode 212 on the second film 203, (5) a step of forming an etching opening (not illustrated) that extends through the second film 203 so as to communicate with the sacrificial layer, and (6) a step of forming a hollow portion by etching the sacrificial layer using a gas containing xenon difluoride and hydrogen via the etching opening.

The second film 203 includes a silicon nitride film. In the silicon nitride film 203, the composition ratio of silicon to nitrogen in a first region 205 having a face in contact with the sacrificial layer is larger than the composition ratio of silicon to nitrogen in a second region 206 not including the first region 205. As in the description for the hollow structure according to this embodiment, the formation of deposits can be suppressed through the above process, which can overcome the etching failure.

The refractive index of the silicon nitride film at a wavelength of 633 nm may be 1.90 or more.

CMUT

The CMUT according to this embodiment includes a first electrode 211, a first film 201 disposed on the first electrode 211, a second film 203 disposed so as to face the first film 201 with a hollow portion 202 formed therebetween, and a second electrode 212 disposed on the second film 203. At least one of the first film 201 and the second film 203 includes a silicon nitride film. In FIG. 25, the second film 203 is a silicon nitride film. In the silicon nitride film 203, the composition ratio of silicon to nitrogen in a first region 205 having a face in contact with the hollow portion 202 is larger than the composition ratio of silicon to nitrogen in a second region 206 not including the first region 205.

The refractive index of the silicon nitride film at a wavelength of 633 nm may be 1.90 or more.

Detailed Description of Embodiments of the Present Invention

Figure 2:
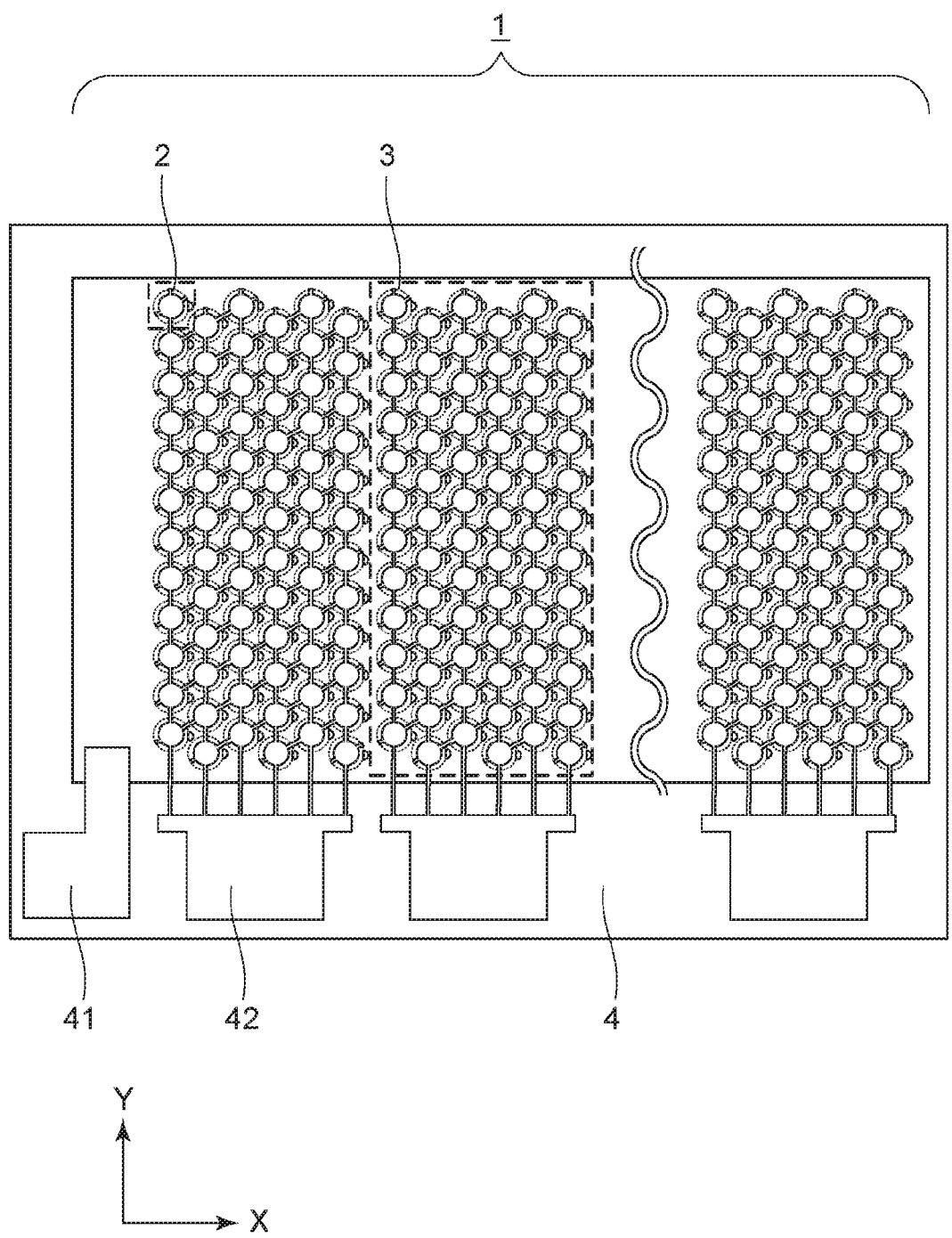
FIG. 2 is an overall view of the CMUT in FIG. 1.
Figure 3:
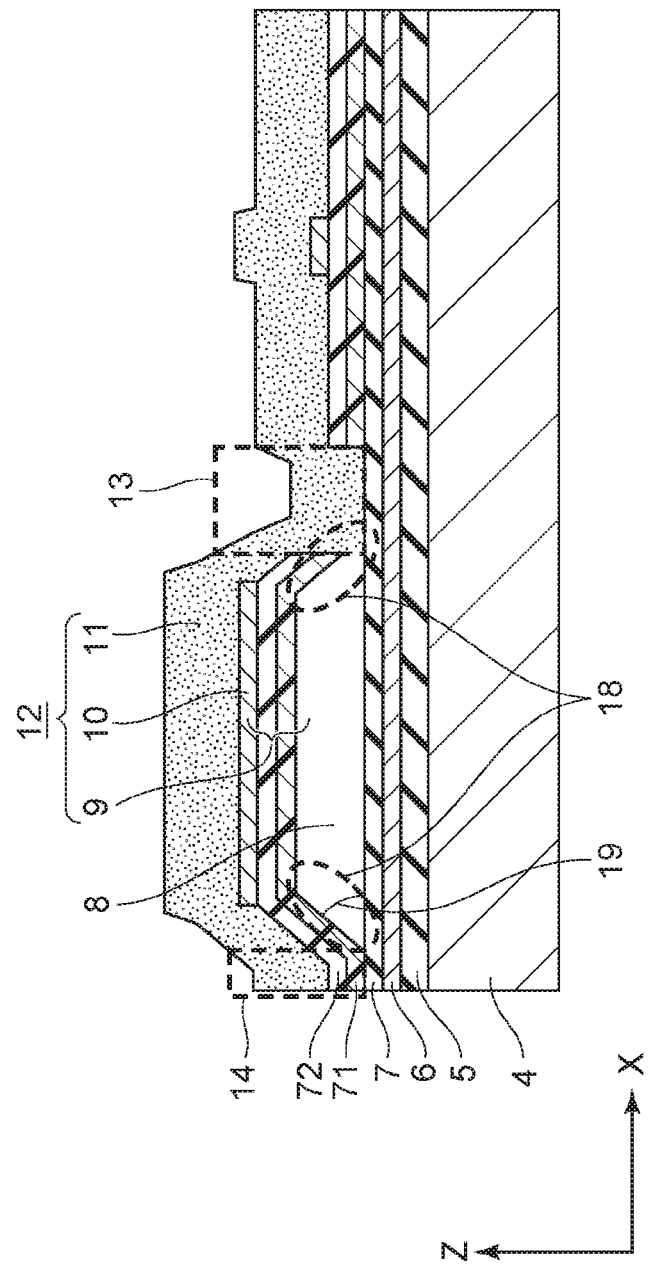
FIG. 3 is a sectional view taken along line A-B of the CMUT in FIG. 1.
Figure 4:
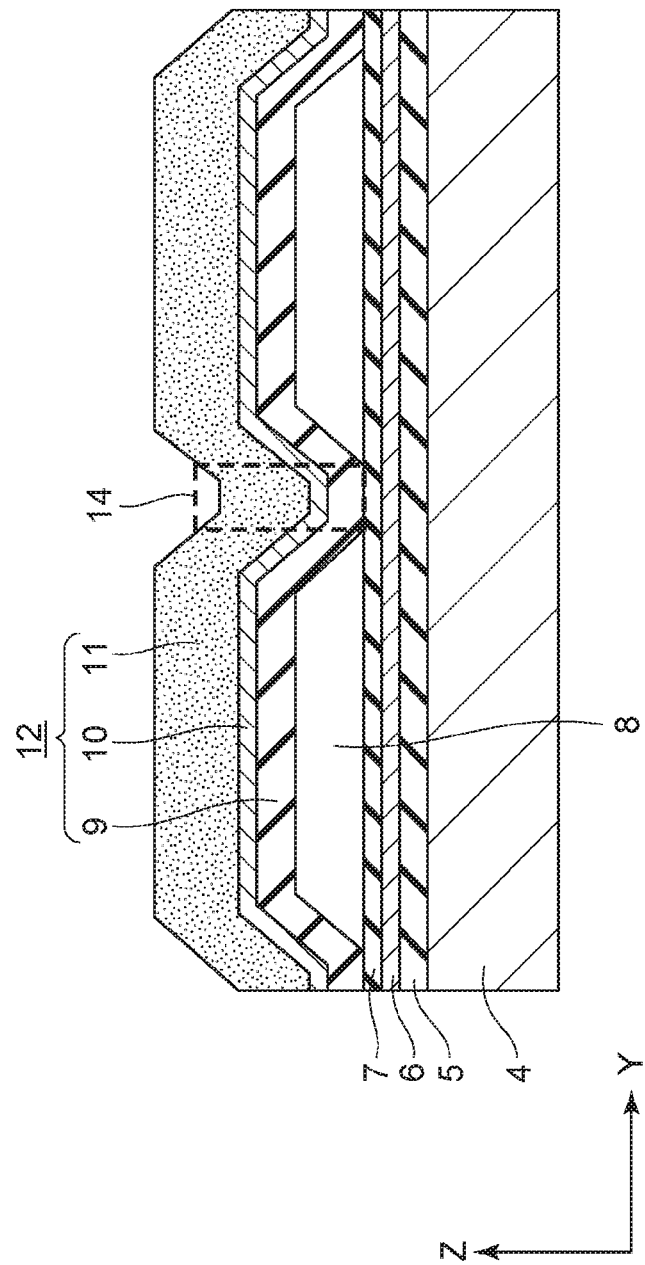
FIG. 4 is a sectional view taken along line C-D of the CMUT in FIG. 1.
Figure 5:
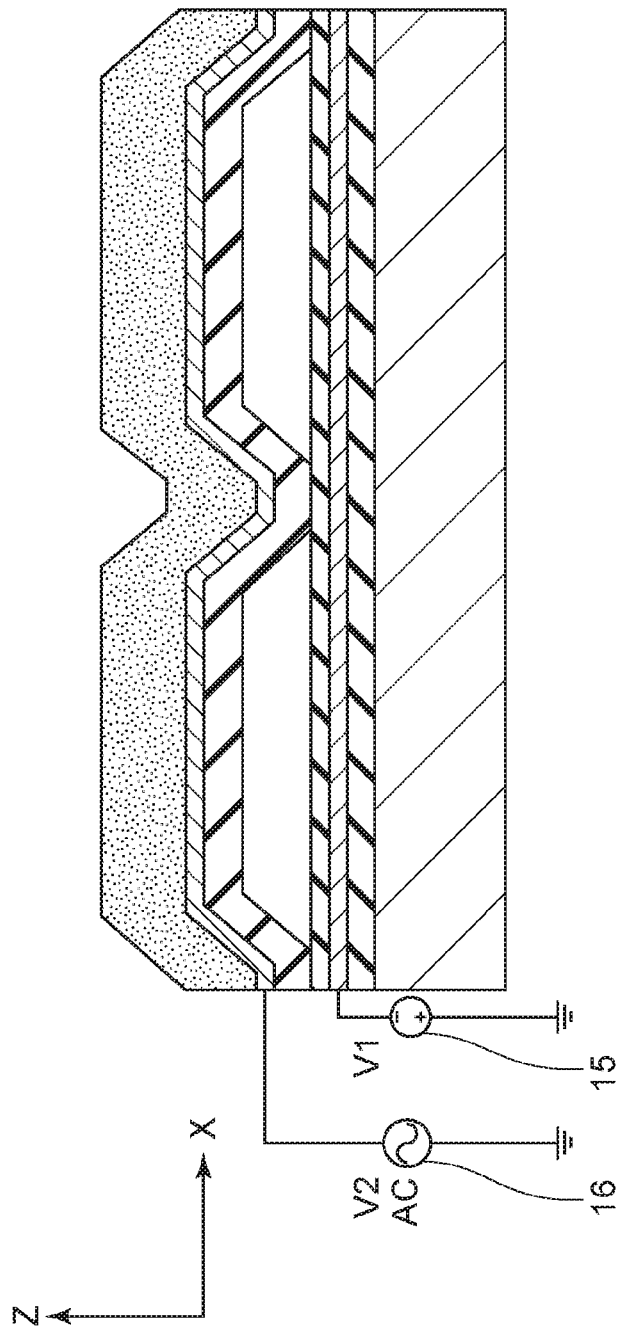
FIG. 5 is a sectional view for describing a method for driving a CMUT.
Figure 6:
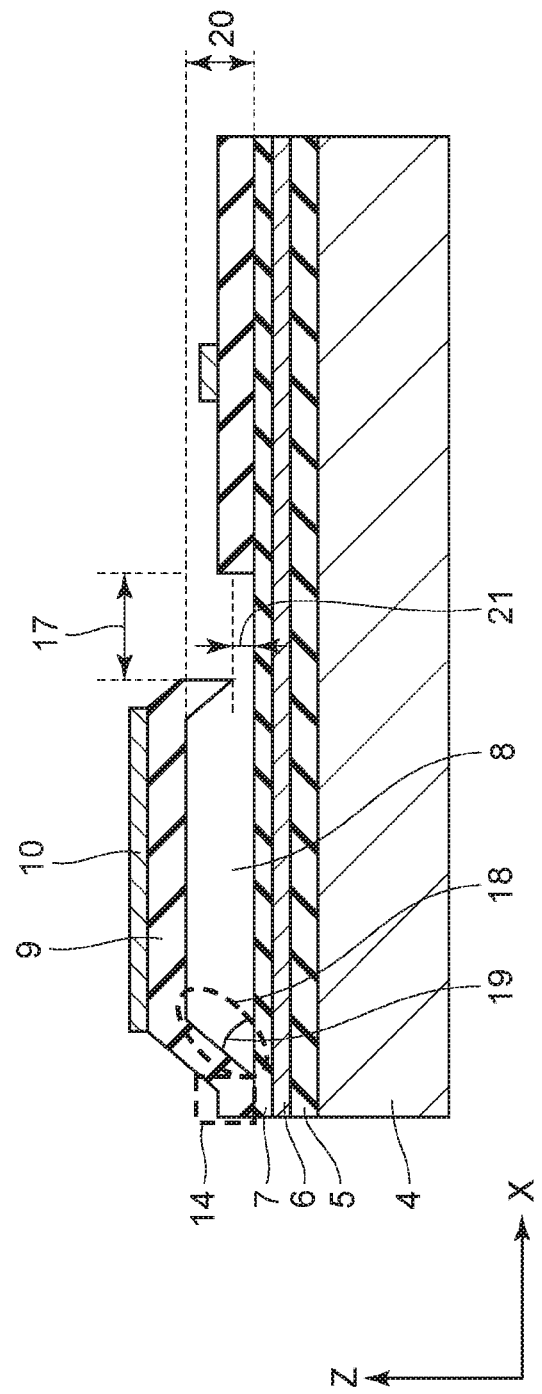
FIG. 6 is a sectional view taken along line A-B after a sacrificial layer is etched in a production process of the CMUT.
Figure 7:
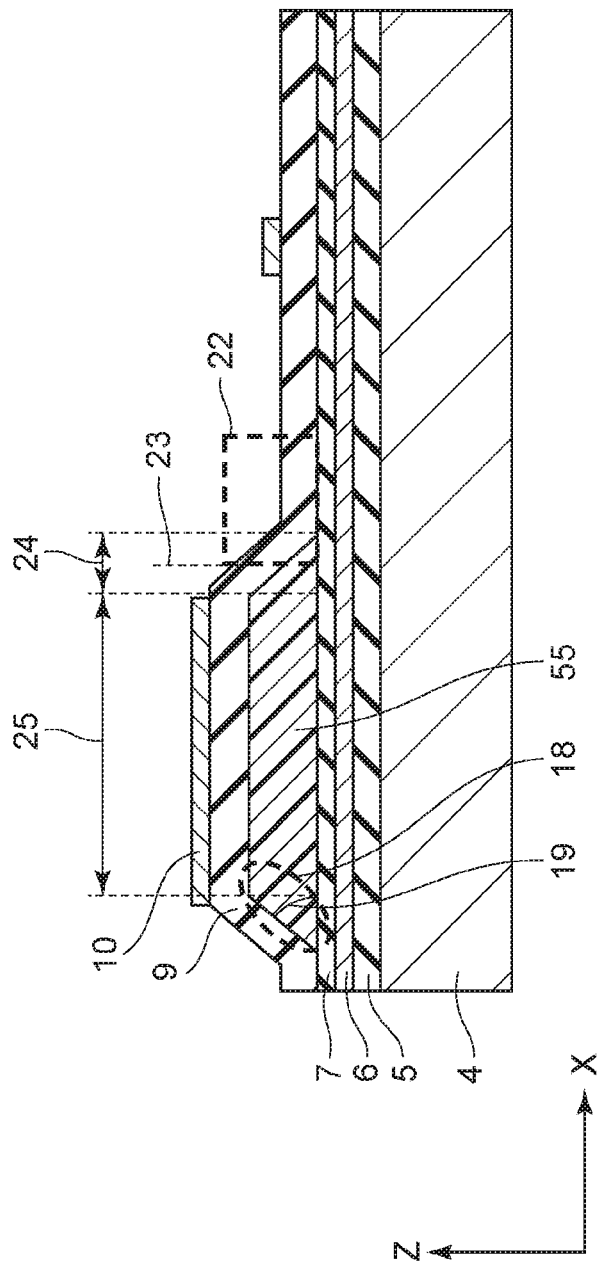
FIG. 7 is a sectional view taken along line A-B before a sacrificial layer is etched in a production process of the CMUT.

Hereafter, the details of the CMUT according to an embodiment of the present invention will be described with reference to FIG. 1 to FIG. 7. FIG. 1 is a top view of a CMUT according to an embodiment of the present invention and FIG. 2 is an overall view of FIG. 1. In FIG. 1, a sealing film 11 is treated as a see-through film to facilitate the understanding. FIG. 3 is a sectional view taken along line A-B in FIG. 1 and FIG. 4 is a sectional view taken along line C-D in FIG. 1. FIG. 5 is a sectional view for describing the driving. FIG. 6 is a sectional view taken along line A-B after a sacrificial layer is etched. FIG. 7 is a sectional view taken along line A-B before a sacrificial layer is etched. In the top views illustrated in this embodiment, a sealing film 11 that is a part of a vibration film 12 is treated as a see-through film.

The reference numerals in the drawings are as follows: 1 denotes a CMUT, 2 denotes a cell, 3 denotes an element, 4 denotes a substrate, 5 denotes a first insulating film, 6 denotes a first electrode, 7 denotes a second insulating film, 8 denotes a hollow portion, 9 denotes a third insulating film, 10 denotes a second electrode, 11 denotes a sealing film, 12 denotes a vibration film, 13 denotes an etching sealing portion, 14 denotes a vibration film supporting portion, 15 denotes a first voltage application unit, 16 denotes a second voltage application unit, 17 denotes an etching opening, 18 denotes a tapered shape, 19 denotes a taper angle, 20 denotes the height of the hollow portion at the vibration film, 21 denotes the height of the hollow portion at the etching opening, 22 denotes a portion in which the etching opening 17 is to be formed, 23 denotes an intermediate position of the tapered shape 18, 24 denotes a distance obtained when the tapered slope is projected on the second insulating film, 25 denotes an opening of the vibration film, 26 denotes an overlapping width, 41 denotes a first electrode pad, 42 denotes a second electrode pad, and 55 denotes a sacrificial layer.

In this embodiment, the third insulating film 9 (first film) is a silicon nitride film and includes a first region 71 having a face in contact with the sacrificial layer (a position indicated by the reference numeral 8) and a second region 72 not including the first region 71. The composition ratio of silicon to nitrogen in the first region 71 is larger than the composition ratio of silicon to nitrogen in the second region 72. In other words, the third insulating film 9 includes a Si-rich silicon nitride film on the hollow portion 8 side and a N-rich silicon nitride film on the second electrode 10 side. Although not illustrated in the drawings below, the third insulating film 9 includes a Si-rich first region 71 on the hollow portion 8 side and a N-rich (a lower Si content than that of the first region) second region 72 on the second electrode 10 side as illustrated in FIG. 3 unless otherwise specified.

In this embodiment, both the first voltage application unit 15 and the second voltage application unit 16 are provided. However, one of the voltage application units may be provided and the other may be connected to a ground (GND).

The CMUT 1 illustrated in FIG. 1 and FIG. 2 is constituted by a first electrode 6 formed on a supporting substrate 4 and a plurality of elements 3 including cells 2 in which the vibration film 12 including a second electrode 10 disposed so as to face the first electrode 6 with a hollow portion 8 formed therebetween is supported while being allowed to vibrate. The CMUT 1 has etching openings 17. The width at which the etching opening 17 and the cell 2 overlap each other is an overlapping width 26.

FIG. 2 illustrates only three elements, but any number of elements may be provided. Each of the elements 3 is constituted by 72 cells 2, but may be constituted by any number of cells 2. The cells may be arranged in any pattern such as a lattice pattern or a staggered pattern. Furthermore, the rough external shape of the elements 3 may be a rectangle illustrated in FIG. 2 or may be a square or a hexagon.

As illustrated in FIG. 1, FIG. 3, and FIG. 4, the cells 2 each include a substrate 4, a first insulating film 5 formed on the substrate 4, a first electrode 6 formed on the first insulating film 5, and a second insulating film 7 formed on the first electrode 6. Furthermore, the third insulating film 9, the second electrode 10, and the sealing film 11 constitute a vibration film 12, and the cells 2 each include a vibration film supporting portion 14 that supports the vibration film 12 and a hollow portion 8. The hollow portion 8, which will be described later, is formed by etching the sacrificial layer via the etching opening 17. The etching opening 17 is sealed with the sealing film 11 in the end to form a sealing portion 13. The etching opening 17 is formed at a position at which the wall surface of the hollow portion 8 has a tapered shape 18 in the process of producing the CMUT 1 described later.

Figure 20:
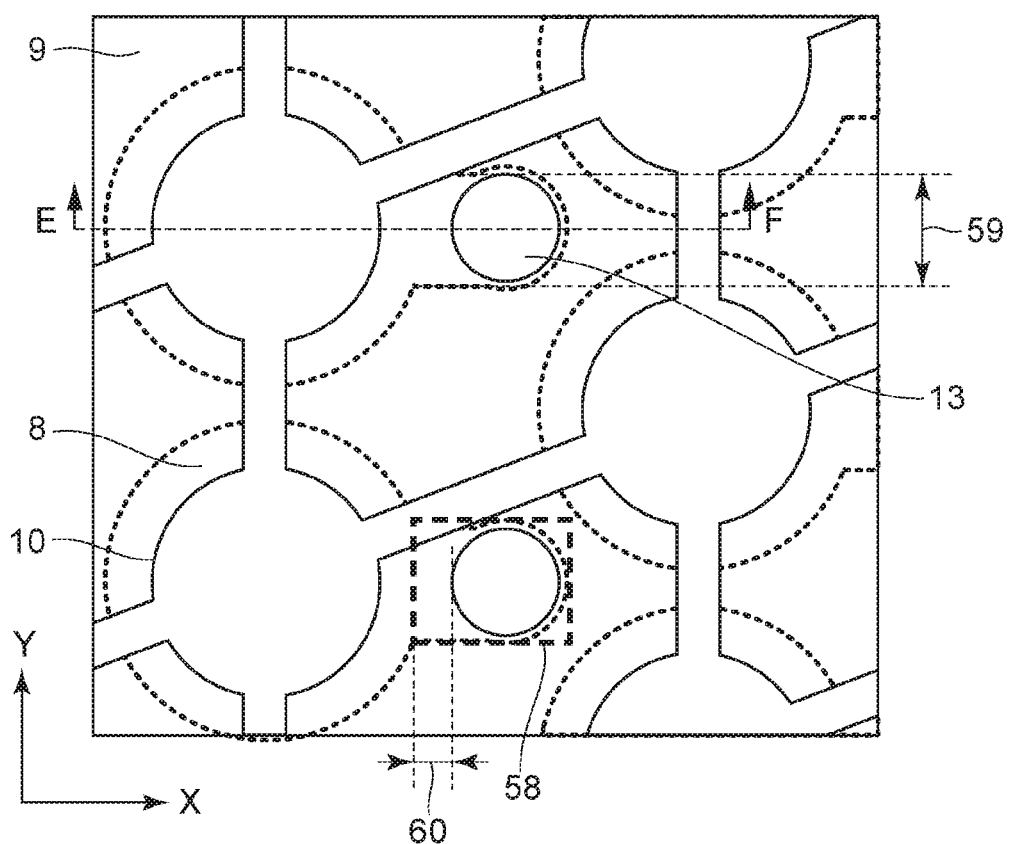
FIG. 20 is a top view for describing a CMUT in which an etching channel is present outside a cell.
Figure 21A:
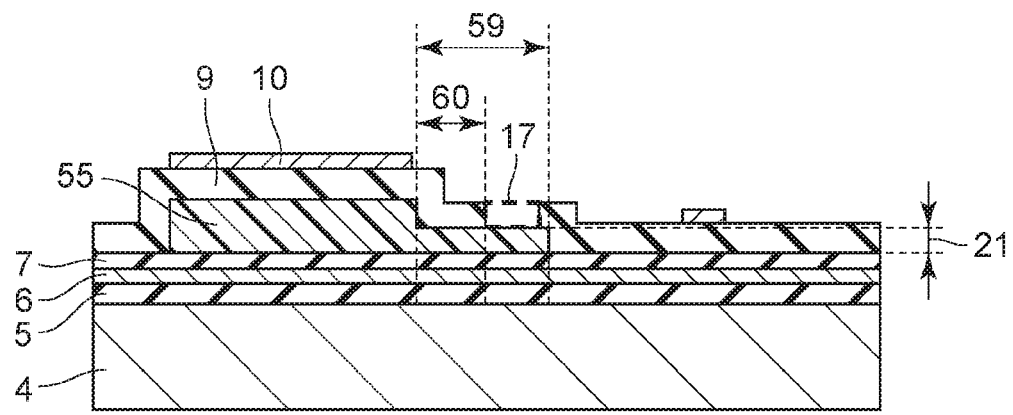
FIG. 21A is a sectional view (a sectional view taken along line E-F in FIG. 20) for describing a method for producing a CMUT in which an etching channel is present outside a cell.
Figure 21B:
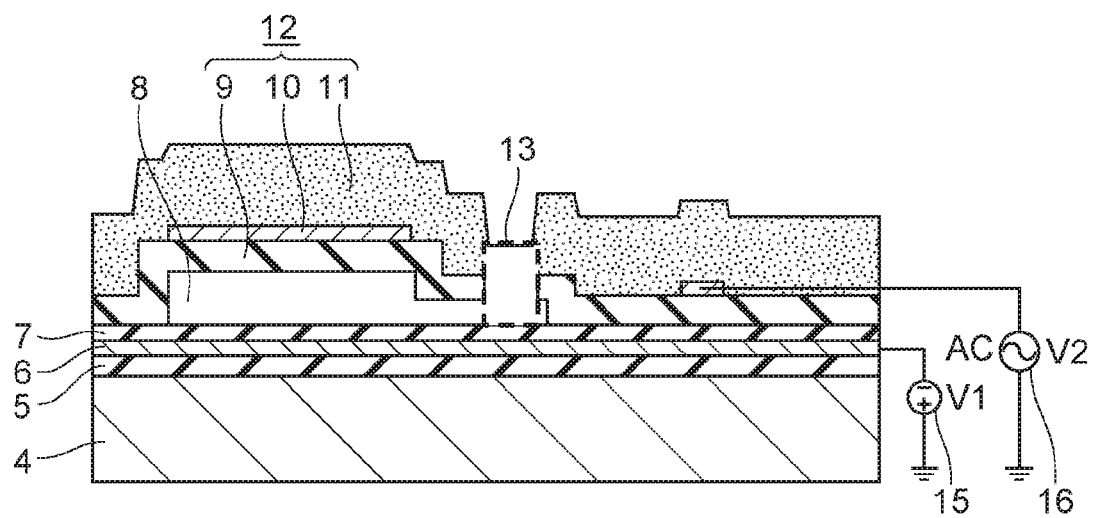
FIG. 21B is a sectional view (a sectional view taken along line E-F in FIG. 20) for describing a method for producing a CMUT in which an etching channel is present outside a cell.

Alternatively, as illustrated in FIG. 20 and FIGS. 21A and 21B, an etching channel may be extended to the outside of the cell and the etching opening may be formed on the channel. FIG. 20 is a schematic enlarged top view of the CMUT 1. FIGS. 21A and 21B are sectional views taken along line E-F in FIG. 20. In the drawings, 58 denotes an etching channel, 59 denotes an etching channel width, and 60 denotes an etching channel length. For the CMUT 1 in FIG. 20, the external dimensions and the external shape, number, and arrangement of the elements 3 are the same as those in FIG. 2. Each of the cells 2 in FIG. 20 has a substantially circular shape. An etching channel 58 is present at the end of the hollow portion 8 of the cell 2, and an etching opening 17 is formed at the end of the etching channel 58. Thus, when the etching opening is sealed, the height of a sacrificial layer at the etching channel that communicates with the etching opening can be made smaller than that of a sacrificial layer corresponding to the hollow portion. This can improve the reliability of sealing.

In this embodiment, the etching opening may have any arrangement. Hereafter, the description will be made using an arrangement in which the etching opening is formed at a position at which the wall surface of the hollow portion 8 has a tapered shape 18.

The etching opening 17 is not illustrated in the top view because the etching opening 17 is sealed with a sealing film 11 and serves as a sealing portion 13 after production of the CMUT 1. The portion in which the second insulating film 7 is seen in the top view is a place where the etching opening 17 has been formed and a place where the sealing portion 13 is formed.

The vibration film supporting portion 14 includes the second electrode 10 to extend a wire or does not include the second electrode 10. When the substrate 4 is an insulating substrate such as a glass substrate, the first insulating film 5 is not necessarily disposed. The second insulating film 7 is disposed to improve the withstand voltage of the cells and prevent the electrification of an insulating film and thus may be omitted if unnecessary. Furthermore, the sealing film 11 is disposed to control the deformation of the vibration film 12 and seal the hollow portion 8 and thus may be omitted if unnecessary. The shape of the hollow portion 8 viewed from above is a substantially circular shape except for the etching sealing portion 13, but may be a shape such as a square or a rectangle.

As illustrated in FIG. 5, the CMUT includes a first voltage application unit 15 that generates a potential difference between the first electrode 6 and the second electrode 10 of the cell 2 and a second voltage application unit 16 that applies a transmission voltage to the second electrode.

In the CMUT according to this embodiment, a bias voltage can be applied to the first electrode 6 using the first voltage application unit 15. When a bias voltage is applied to the first electrode 6, a potential difference is generated between the first electrode 6 and the second electrode 10.

This potential difference displaces the vibration film 12 to a position at which the restoring force of the vibration film and the electrostatic attraction are balanced. When ultrasonic waves reach the vibration film 12 in this state, the capacitance between the first electrode 6 and the second electrode 10 changes through vibration of the vibration film 12, which allows an electric current to flow through the second electrode 10. By extracting the electric current through the second electrode pad 42 extended from the second electrode 10, the ultrasonic waves can be extracted as electric signals.

When a transmission driving voltage is applied to the second electrode 10 from the second voltage application unit 16 while a bias voltage is applied to the first electrode 6 from the first voltage application unit 15, the ultrasonic waves can be transmitted. The transmission driving voltage may have any waveform as long as the waveform is capable of transmitting desired ultrasonic waves. A desired waveform such as a unipolar pulse, a bipolar pulse, a burst wave, or a continuous wave may be used.

Next, the etching opening 17 and the tapered shape 18 will be described with reference to FIG. 6 and FIG. 7. In this embodiment, as illustrated in FIG. 6, the wall surface of the hollow portion 8 has a tapered shape 18 toward the first electrode, and the etching opening 17 for forming the hollow portion 8 is formed at a position at which the wall surface of the hollow portion 8 has a tapered shape 18. As illustrated in FIG. 3, the etching sealing portion 13 is formed at a position at which the wall surface of the hollow portion 8 has a tapered shape 18. By forming the etching opening 17 at a position at which the wall surface of the hollow portion 8 has a tapered shape 18, the etching opening 17 can be located near the center of a sacrificial layer 55. Therefore, the etching of the sacrificial layer 55 can be completed within a short time. The height 21 of the hollow portion at the etching opening 17 can be made smaller than the height 20 of the hollow portion at the vibration film. This can reduce the thickness of the sealing film 11 required to seal the hollow portion 8. Thus, a thin vibration film 12 can be formed with high reliability of sealing.

FIG. 7 is a sectional view taken along line A-B immediately before the etching opening 17 is formed. A sacrificial layer 55 is formed in a portion in which the hollow portion 8 is to be formed after the sacrificial layer etching. The portion enclosed by a broken line 22 is a portion in which the etching opening 17 is to be formed. The etching opening 17 needs to be formed so as to overlap a portion having the tapered shape 18 with certainty. Therefore, the position and shape of the etching opening 17 may be determined in consideration of the alignment precision of an exposure device used to form the etching opening 17.

For example, when the etching sealing portion 13 has a semicircular shape as illustrated in FIG. 1, the etching opening 17 also has a similar semicircular shape. Therefore, the etching opening 17 may be formed such that the outer periphery of the etching opening 17 partly overlaps the slope of the tapered shape 18. Herein, the etching opening 17 is formed in consideration of the alignment precision of an exposure device such that the outer periphery of the etching opening 17 always partly overlaps the slope of the tapered shape 18. If the outer periphery of the etching opening 17 does not partly overlap the slope of the tapered shape 18 because of, for example, misalignment of the exposure device, it is highly likely that the sacrificial layer etching described later cannot be performed. For example, when the alignment precision of the exposure device is ±50 nm, the distance 24 (the length obtained when the tapered shape 18 is projected on the second insulating film 7) between broken lines may be set to more than 100 nm.

By forming the etching opening 17 such that the outer periphery of the etching opening 17 (the end of a portion enclosed by a dotted line 22) partly overlaps a broken line 23 that indicates the intermediate position of the tapered shape 18, the sacrificial layer etching can be performed with certainty. The reference numeral 25 in the drawing denotes an opening 25 of the vibration film 12. The size of the opening 25 determines the frequency characteristics of the vibration film 12, and the total area of the openings 25 of the cells 2 constituting the elements 3 determines the reception sensitivity and the transmission efficiency.

Figure 8:
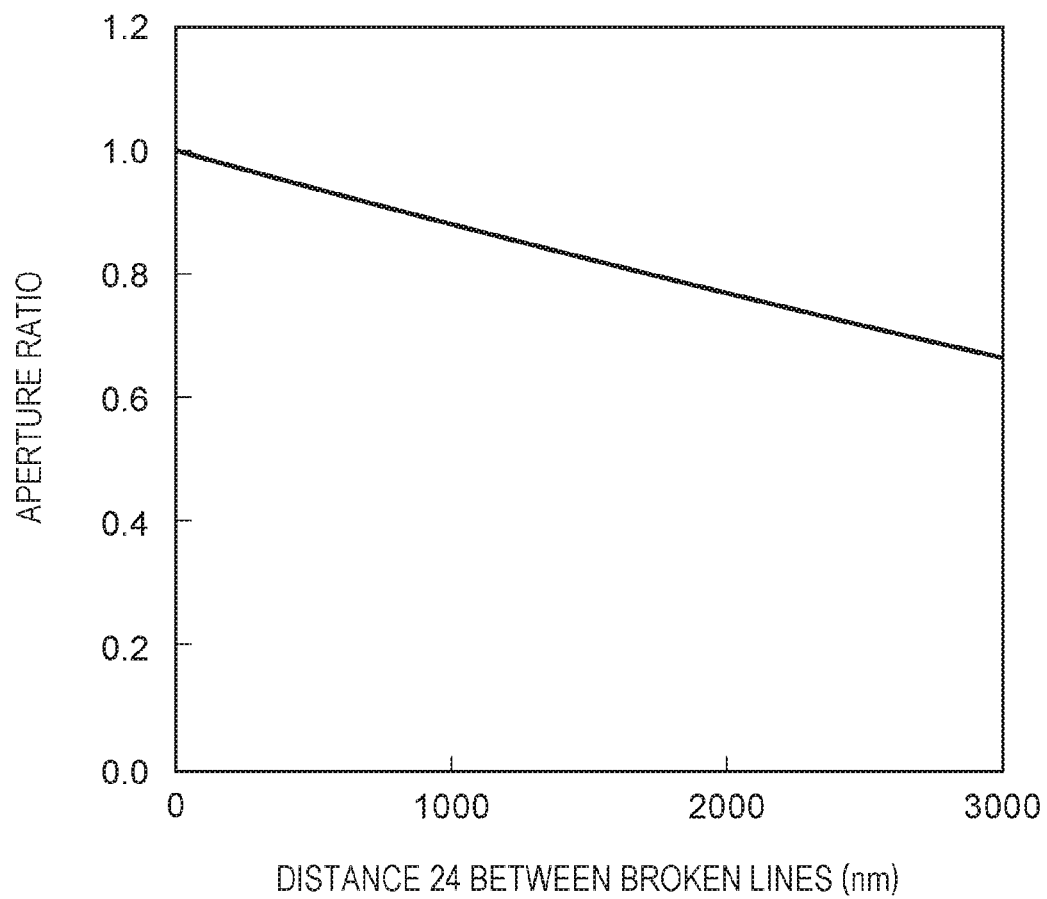
FIG. 8 is a graph illustrating the relationship between a distance between broken lines and an aperture ratio for describing the CMUT according to an embodiment of the present invention.

FIG. 8 illustrates the relationship between the distance 24 between the broken lines and the aperture ratio. In FIG. 8, the horizontal axis shows the distance 24 between the broken lines and the vertical axis shows the aperture ratio of the openings 25 of the cells 2 constituting the elements 3. As illustrated in FIG. 8, the aperture ratio decreases as the distance 24 between the broken lines increases. Therefore, the distance 24 between the broken lines may be decreased by decreasing the value of the alignment precision of the exposure device.

Figure 9:
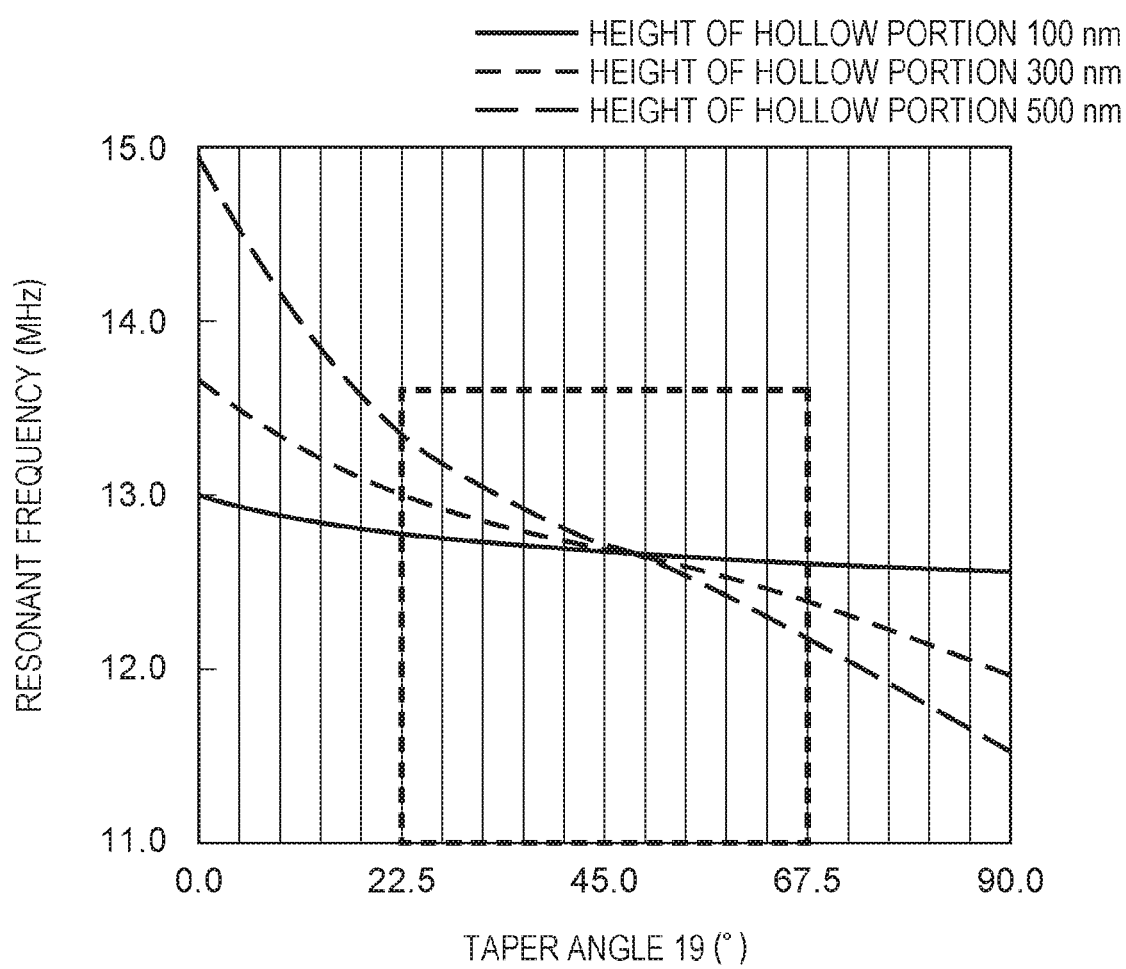
FIG. 9 is a graph illustrating the relationship between a taper angle and a resonant frequency of a vibration film for describing the CMUT according to an embodiment of the present invention.

FIG. 9 illustrates the relationship between the taper angle 19 and the resonant frequency of the vibration film 12. In FIG. 9, the horizontal axis shows the taper angle 19 between the inner wall of the hollow portion 8 and the second insulating film 7, and the vertical axis shows the resonant frequency of the vibration film 12 included in each of the cells 2 constituting the elements 3. The series is the height 20 of the hollow portion at the vibration film, ranging from 100 nm to 500 nm, which is the height of a hollow portion formed in typical CMUTs. As illustrated in FIG. 9, since the resonant frequency varies depending on the taper angle 19 and the height of 20 of the hollow portion, the taper angle 19 may be determined such that the influence due to the variation is reduced. When the height 20 of the hollow portion is 500 nm, the variation in resonant frequency increases at a taper angle 19 of 22.5° or less. When the height 20 of the hollow portion is 300 nm, the variation in resonant frequency increases at a taper angle 19 of more than 67.5°. Thus, the taper angle 19 may be in the range of 22.5° to 67.5°.

Figure 10:
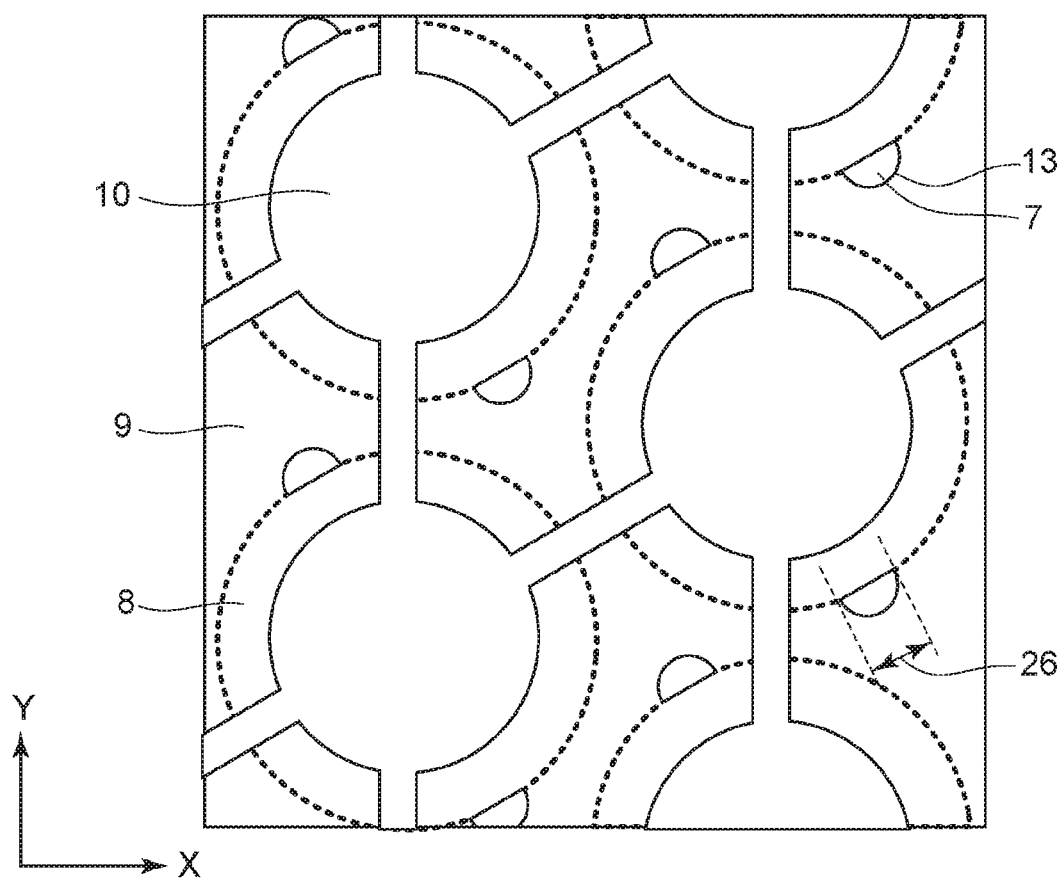
FIG. 10 illustrates an example of a cell arrangement of the CMUT according to an embodiment of the present invention.

FIG. 10 to FIG. 13 are enlarged top views of elements 3 whose etching sealing portions 13 have different arrangements and shapes. In the drawings, the sealing film 11 that is a part of the vibration film 12 is treated as a see-through film for the sake of convenience. The reference numeral 26 in the drawings denotes an overlapping width at which the outer periphery of the cell and the etching sealing portion 13 overlap each other. In the top views, the portion in which the second insulating film 7 is seen is a place where the etching opening 17 has been formed and a place where the sealing portion 13 is formed. The reference numeral 26 in the drawings also denotes an overlapping width at which the outer periphery of the cell and the etching opening 17 overlap each other. The size of the etching opening 17 may be determined in accordance with the position of the etching opening 17, the number of etching openings 17, the minimum patterning precision, and the desired etching time. One etching opening 17 may be formed in each cell as illustrated in FIG. 1 or two or more etching openings 17 may be formed in each cell as illustrated in FIG. 10. When two or more etching openings 17 are formed, the etching openings 17 may be arranged such that the sacrificial layer etching isotropically proceeds in the cell 2 to reduce the variation in the height 20 of the hollow portion 8. As illustrated in FIG.

Figure 12:
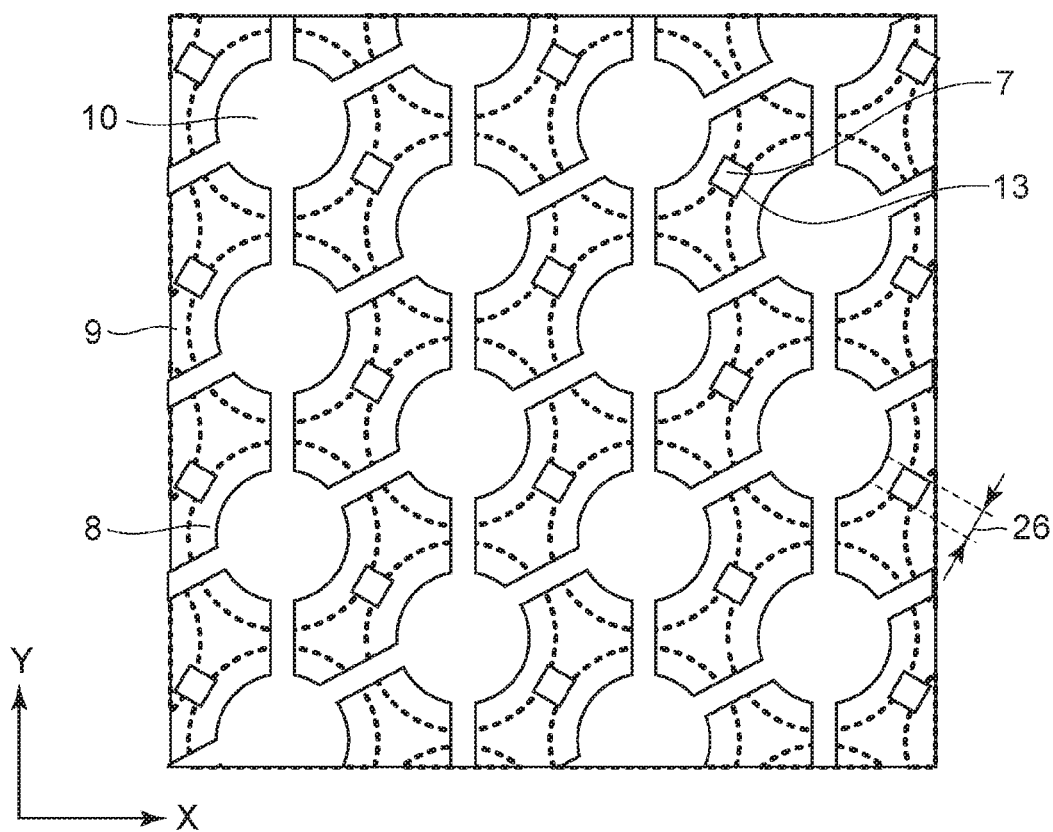
FIG. 12 illustrates an example of a cell arrangement of the CMUT according to an embodiment of the present invention.

11, one etching opening 17 may be formed for a plurality of cells. As illustrated in FIG. 12, a plurality of etching openings 17 may be formed for a plurality of cells.

Figure 11:
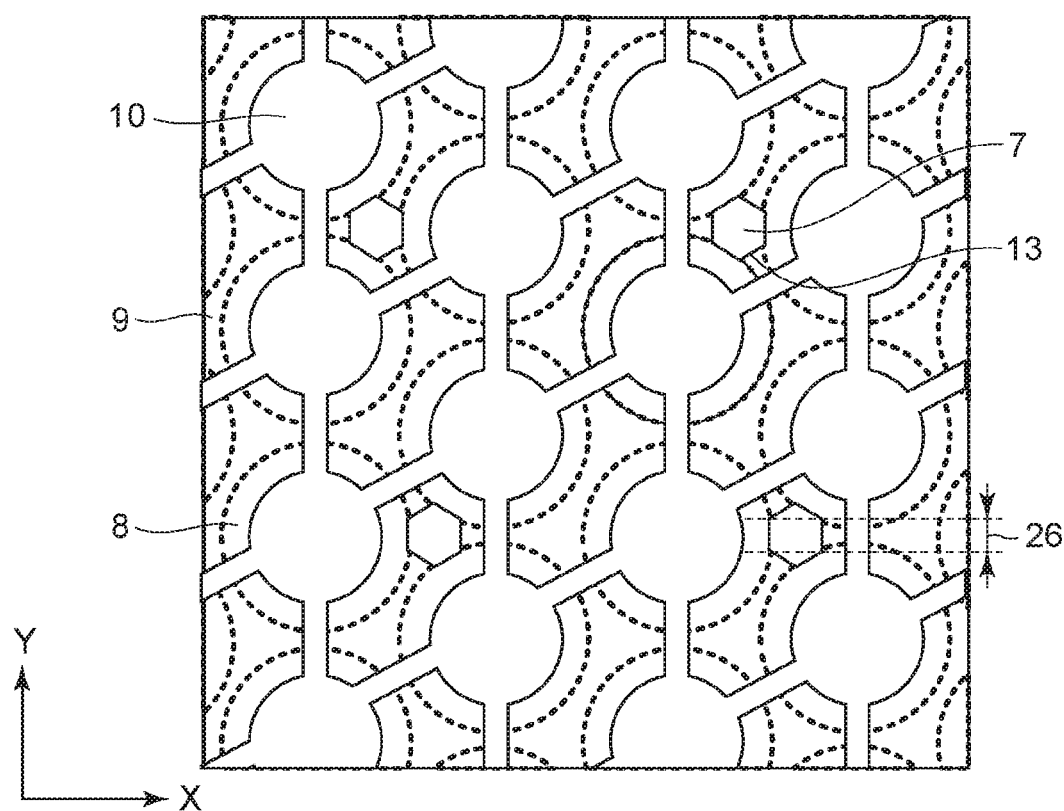
FIG. 11 illustrates an example of a cell arrangement of the CMUT according to an embodiment of the present invention.
Figure 13:
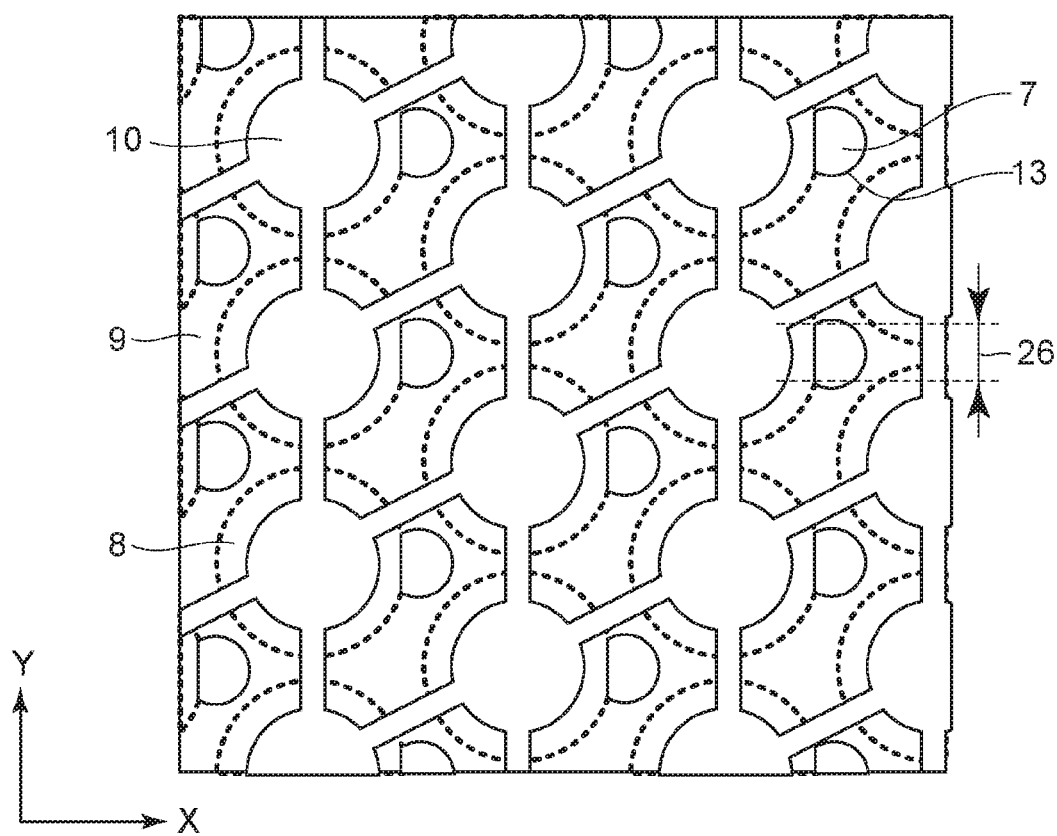
FIG. 13 illustrates an example of a cell arrangement of the CMUT according to an embodiment of the present invention.

FIG. 13 illustrates an arrangement in which one etching opening 17 is formed in each cell having the same size as that in FIG. 11 and FIG. 12. In FIG. 13, the etching opening 17 is arranged so as not to communicate with the adjacent cells. Thus, even if sealing failure is caused in some of the cells, the influence of the sealing failure does not spread to the adjacent cells. However, the etching opening 17 needs to be arranged so as not to communicate with the adjacent cells in consideration of the alignment precision of an exposure device used to form the etching opening 17. Therefore, the cells 2 cannot be arranged at a higher density. When the etching opening 17 is formed for some of the cells as illustrated in FIG. 11 and FIG. 12, the cells 2 can be arranged at a higher density, which can increase the total area of the openings 25 of the vibration films 12 of the cells 2 constituting the elements 3. Furthermore, even if sealing failure is caused in some of the cells, the influence of the sealing failure can be kept in a certain region.

For example, the case where the cell diameter is 32 µm, the minimum patterning precision of the sacrificial layer is 3 µm, and the alignment precision of an exposure device is ±50 nm in the arrangement illustrated in FIG. 11 will be discussed. When the etching opening 17 has a hexagonal shape, the size of the etching opening 17 may be set such that the diameter of the circumcircle is more than 8.55 µm and the circumcircle is present on the slope of the tapered shape 18. When the etching opening 17 is formed such that the outer periphery of the etching opening 17 partly overlaps the slope of the tapered shape 18, a long sacrificial layer etching time is required at a small overlapping width 26 and the performance of the vibration film is changed at a large overlapping width 26. Therefore, the overlapping width 26 may be determined in consideration of the balance between the etching time and the performance.

Figure 14:
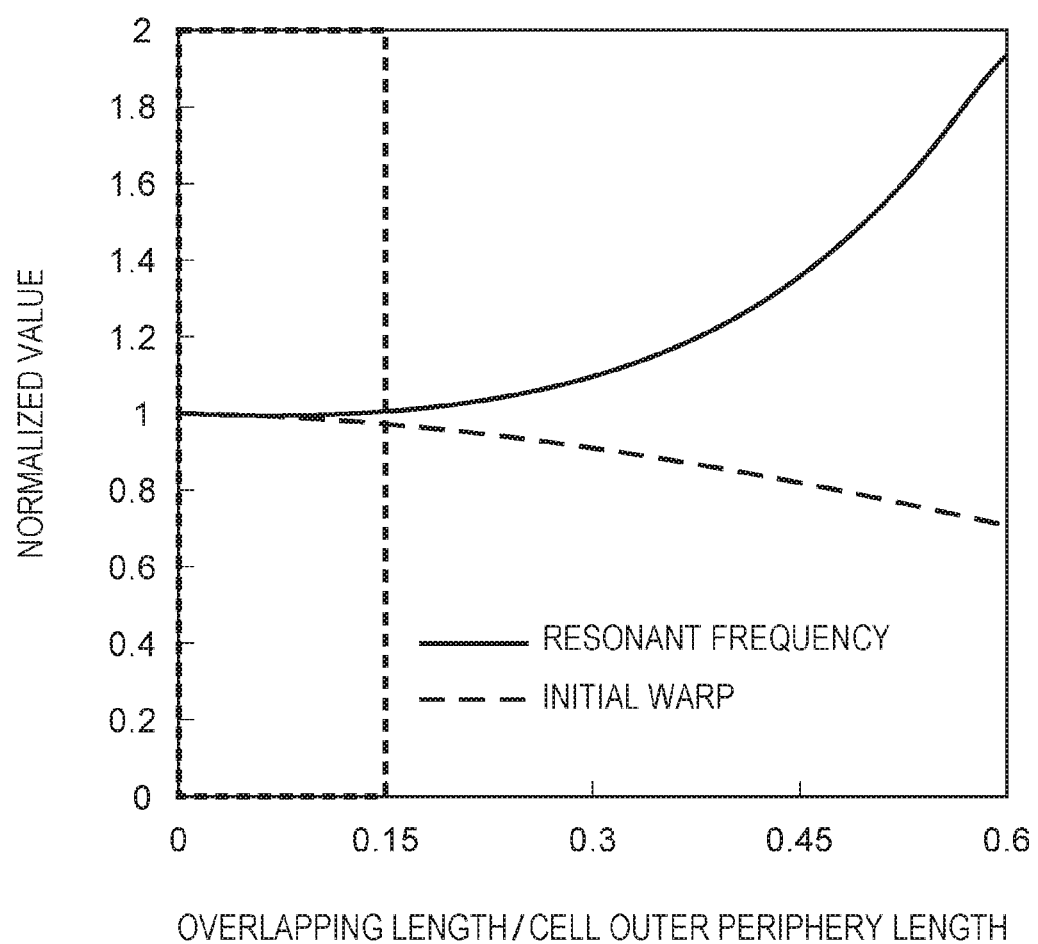
FIG. 14 is a graph illustrating the relationship between the overlapping length/cell outer periphery length and the resonant frequency and initial warp of a vibration film of the CMUT according to an embodiment of the present invention.

FIG. 14 illustrates the relationship between the ratio of the length of the overlapping width 26 to the length of the outer periphery of the cell and the resonant frequency and initial warp of the vibration film 12. The length of the overlapping width 26 is a total length of the overlapping widths 26 of the etching openings 17 formed in one of the cells 2. In FIG. 14, the horizontal axis shows a value obtained by dividing the length of the overlapping width 26 by the length of the outer periphery of the cell, and the vertical axis shows the resonant frequency and initial warp of the vibration film 12 that are normalized at an overlapping width 26 of 0. For the series, a solid line indicates the resonant frequency and a broken line indicates the initial warp. The initial warp refers to a displacement of the vibration film 12 in the negative Z-axis direction while a driving voltage is not applied to the CMUT 1 in the air.

As illustrated in FIG. 14, when the ratio of the length of the overlapping width 26 to the length of the outer periphery of the cell increases, the area of the vibration film supporting portion including the sealing portion 13 increases, which increases the resonant frequency and decreases the initial warp. When the length of the overlapping width 26 varies, the ratio may be selected within a range in which changes in resonant frequency and initial warp are small. The value obtained by dividing the length of the overlapping width 26 to the length of the outer periphery of the cell may be in the range of more than 0 and 0.15 or less, which is the range enclosed by a dotted line in FIG. 14. The shape of the etching opening 17 may be a shape other than the semicircular shape, such as a circular shape or a polygonal shape.

The etching opening 17 is sealed with a sealing film 11 after the sacrificial layer etching. The sealing film 11 is a part of the vibration film 12, and the thickness of the sealing film 11 affects the frequency characteristics of the elements 3. Therefore, the etching opening 17 needs to be sealed with a sealing film 11 having a desired thickness. Accordingly, the taper angle 19 and the arrangement and size of the etching opening 17 are determined such that the etching opening 17 can be sealed with a sealing film 11 having a desired thickness.

Driving Device

Figure 15:
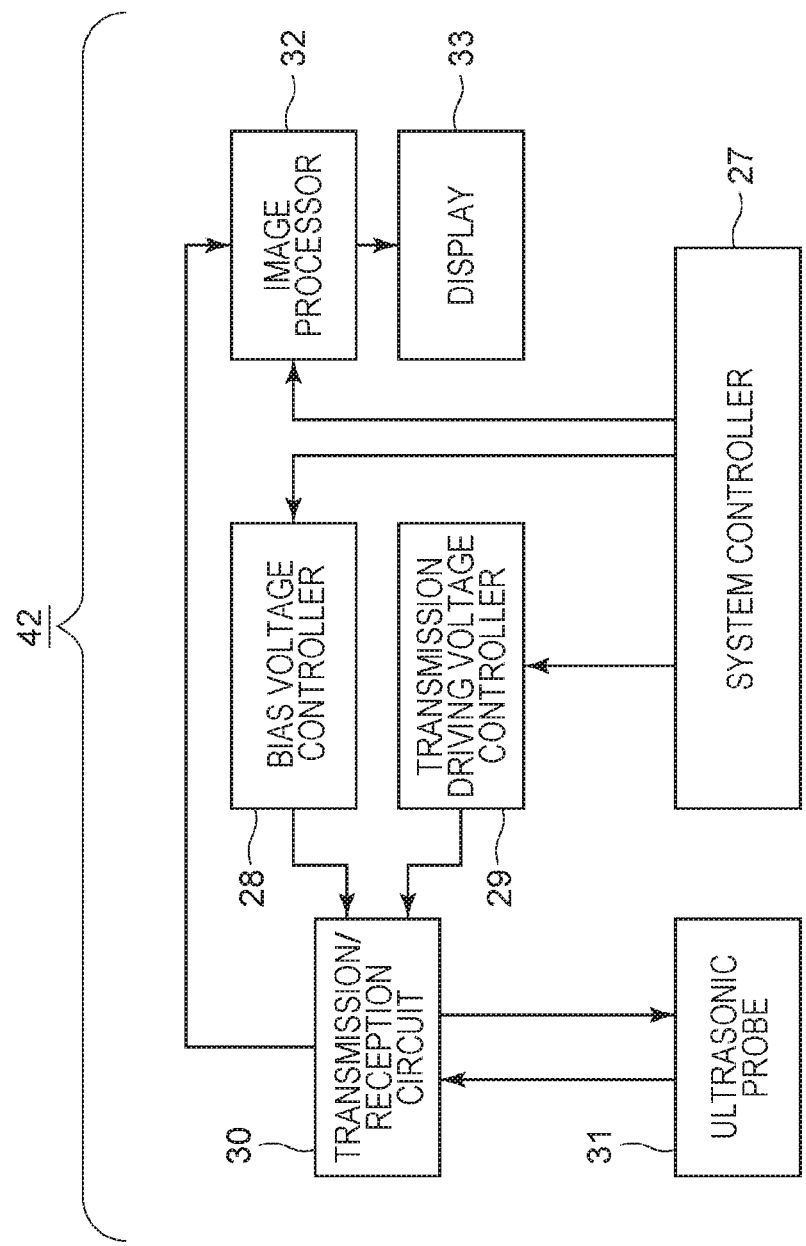
FIG. 15 illustrates an example of a driving device of the CMUT according to an embodiment of the present invention.

FIG. 15 illustrates an example of a driving device. A driving device 42 includes a system controller 27, a bias voltage controller 28, a transmission driving voltage controller 29, a transmission/reception circuit 30, an ultrasonic probe 31, an image processor 32, and a display 33. The ultrasonic probe 31 includes a CMUT 1 that transmits ultrasonic waves to a subject and receives ultrasonic waves reflected from the subject. The transmission/reception circuit 30 is a circuit that supplies, to the ultrasonic probe 31, a bias voltage and a transmission driving voltage supplied from the outside and that processes the ultrasonic waves received by the ultrasonic probe 31 and outputs the processed data to the image processor 32.

The bias voltage controller 28 supplies a bias voltage to the transmission/reception circuit 30 in order to supply the bias voltage to the ultrasonic probe 31. The bias voltage controller 28 includes a power supply and a switch that are not illustrated and supplies a bias voltage to the transmission/reception circuit 30 at a timing instructed by the system controller 27. The transmission driving voltage controller 29 supplies a transmission driving voltage to the transmission/reception circuit 30 in order to supply the transmission driving voltage to the ultrasonic probe 31. At a timing instructed by the system controller 27, a waveform that provides desired frequency characteristics and the transmission sound pressure level is supplied to the transmission/reception circuit 30.

The image processor 32 performs image conversion (e.g., B-mode image and M-mode image) using signals output from the transmission/reception circuit 30 and outputs image signals to the display 33. The display 33 is a display device that displays the image signals output from the image processor 32. The display 33 may be provided separately from the driving device 42. The system controller 27 is a circuit that controls, for example, the bias voltage controller 28, the transmission driving voltage controller 29, and the image processor 32.

Transmission/Reception Circuit of Ultrasonic Waves

Figure 16:
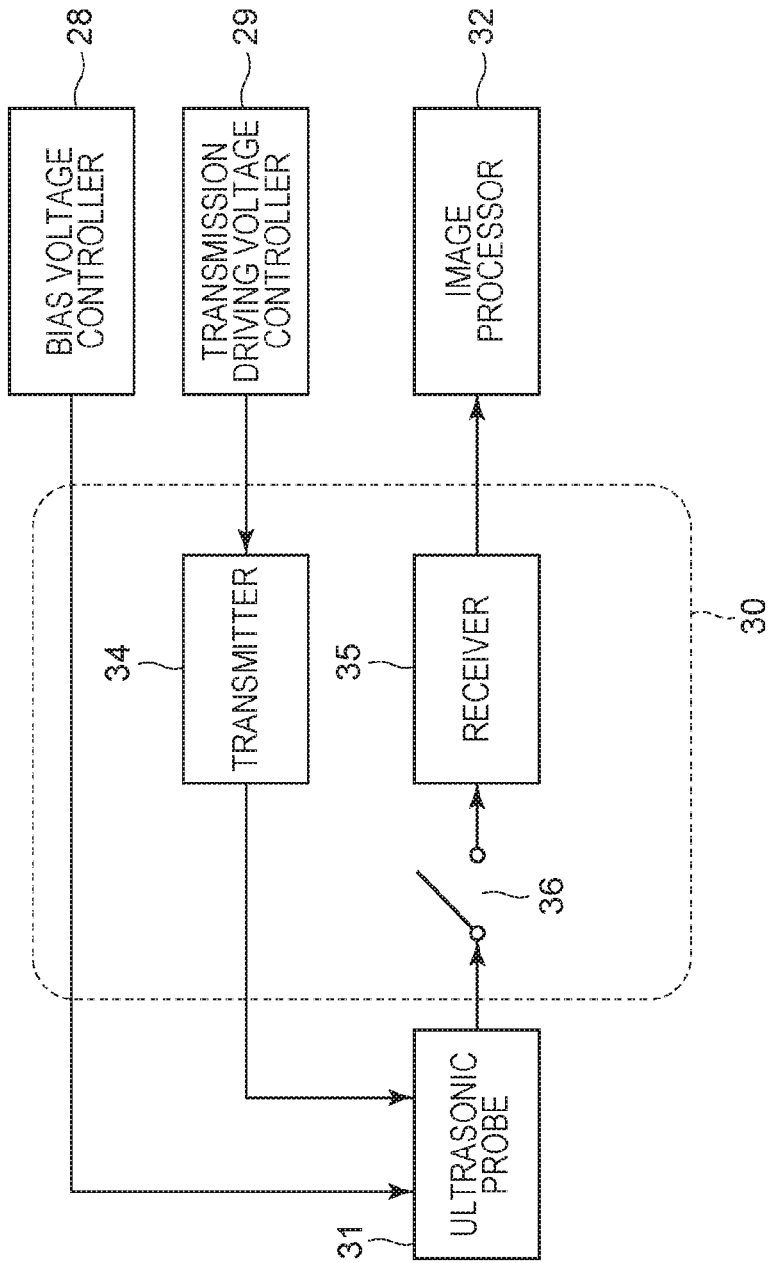
FIG. 16 illustrates an example of a transmission/reception circuit for driving the CMUT according to an embodiment of the present invention.

FIG. 16 illustrates an example of the transmission/reception circuit 30. The transmission/reception circuit 30 includes a transmitter 34, a receiver 35, and a switch 36. When a transmission operation is performed, the transmission/reception circuit 30 applies, to the ultrasonic probe 31, a bias voltage applied from the bias voltage controller 28 in accordance with the transmission bias voltage instructed by the system controller 27 in FIG. 15. Similarly, the transmission/reception circuit 30 applies, to the ultrasonic probe 31 via the transmitter 34, a voltage applied from the transmission driving voltage controller 29 in accordance with the transmission voltage instructed by the system controller 27. When a transmission driving voltage is applied, the switch 36 is opened to prevent signals from flowing to the receiver 35. When a transmission driving voltage is not applied, the switch 36 is closed to provide a reception state. The switch 36 is constituted by, for example, a diode (not illustrated) and serves as a protection circuit for preventing the receiver 35 from being broken. When ultrasonic waves transmitted from the ultrasonic probe 31 are reflected by the subject and returned to the ultrasonic probe 31, the ultrasonic probe 31 receives the ultrasonic waves. Upon reception of ultrasonic waves, a bias voltage applied from the bias voltage controller 28 is applied to the ultrasonic probe 31 in accordance with the reception bias voltage instructed by the system controller 27 in FIG. 15. Since the switch 36 is close, the received signals are amplified by the receiver 35 and sent to the image processor 32.

Figure 17:
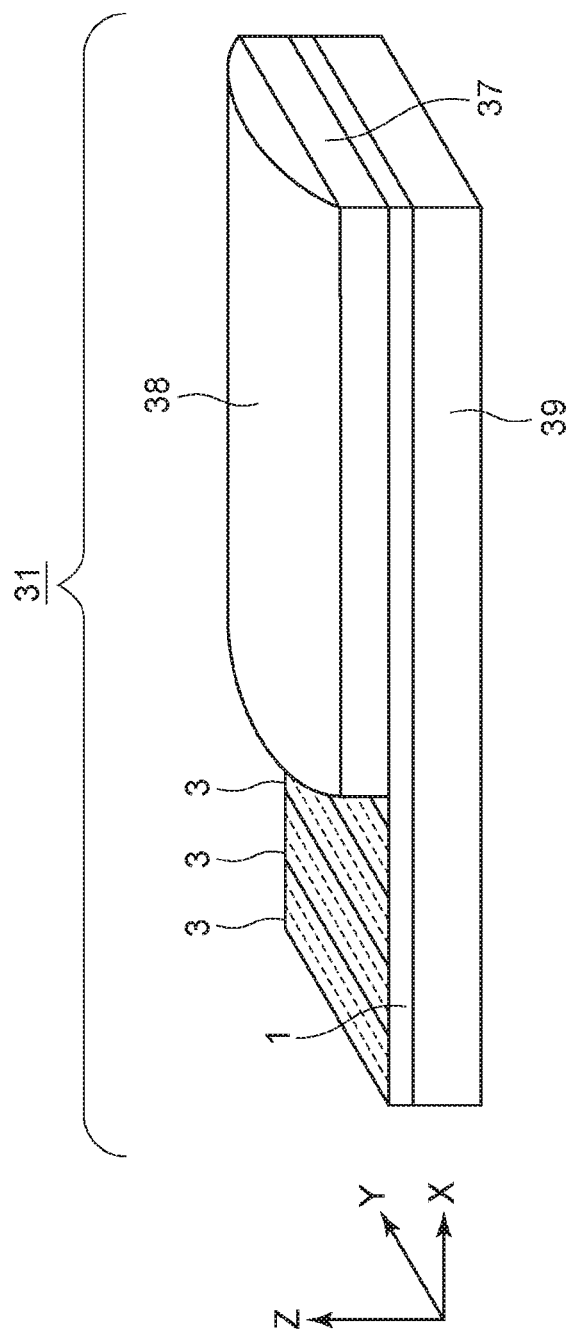
FIG. 17 illustrates an example of an ultrasonic probe according to an embodiment of the present invention.

FIG. 17 is a perspective view illustrating an example of the ultrasonic probe 31. The ultrasonic probe 31 includes a capacitive micromachined ultrasonic transducer 1, an acoustic matching layer 37, an acoustic lens 38, and a circuit board 39. In the capacitive micromachined ultrasonic transducer 1 in FIG. 17, many elements 3 are arranged in a one-dimensional array in an X direction as illustrated in FIG. 17. The elements 3 are arranged in a one-dimensional array in FIG. 17, but may be arranged in a two-dimensional array, or another arrangement such as a convex arrangement may be employed.

The CMUT 1 is mounted on the circuit board 39 in an electrically connected manner. The circuit board 39 may be integrated with the transmission/reception circuit 30 illustrated in FIG. 16, or the CMUT 1 may be connected to the transmission/reception circuit 30 illustrated in FIG. 16 through the circuit board 39. The acoustic matching layer 37 provided for acoustic impedance matching for the subject is disposed on the front side of the CMUT 1 from which ultrasonic waves are transmitted. The acoustic matching layer 37 may be disposed as a protective film for preventing the current leakage to the subject. The acoustic lens 38 is disposed on the acoustic matching layer 37. The acoustic lens 38 may be an acoustic lens that can achieve acoustic impedance matching between the subject and the acoustic matching layer 37.

When the acoustic lens 38 having a curvature in a Y direction as illustrated in FIG. 17 is disposed, ultrasonic waves spread in the Y direction can be converged at the focal point of the acoustic lens. Ultrasonic waves themselves spread in the X direction cannot be converged. Therefore, by performing the transmission operation with beamforming by shifting the timing at which ultrasonic waves are transmitted for each of the elements 3, the ultrasonic waves can be converged at the focal point. The acoustic lens 38 may have a shape in which desired distribution characteristics of ultrasonic waves can be obtained. The type and shape of the acoustic matching layer 37 and the acoustic lens 38 may be selected in accordance with the type of subject used, or the acoustic matching layer 37 and the acoustic lens 38 may be omitted. The bias voltage and the transmission driving voltage to the ultrasonic probe 31 are supplied to the transmission/reception circuit 30 through a cable (not illustrated). The received signals of ultrasonic waves reflected from the subject are transmitted to the image processor 32 through a cable (not illustrated).

Method for Producing CMUT

Figure 18A:
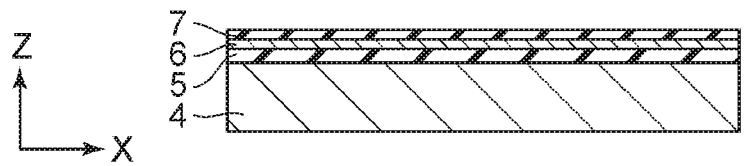
FIG. 18A is a sectional view (a sectional view taken along line A-B in FIG. 1) for describing a method for producing a CMUT according to an embodiment of the present invention.

Next, an example of a method for producing a CMUT 1 having a hollow structure according to this embodiment will be described with reference to FIGS. 18A to 18G. FIGS. 18A to 18G are sectional views taken along line A-B in FIG. 1. As illustrated in FIG. 18A, a first insulating film 5 is formed on a substrate 4. The substrate 4 is a silicon substrate, and the first insulating film 5 is disposed to insulate the substrate 4 and a first electrode 6. When the substrate 4 is an insulating substrate such as a glass substrate, the first insulating film 5 is not necessarily formed. The substrate 4 may be a substrate having a low surface roughness. If the surface roughness is high, the surface roughness is also transferred in a film formation process performed after this process, and the distance between the first electrode 6 and the second electrode 10 varies among cells because of the surface roughness. This variation results in a variation in conversion efficiency, which leads to variations in sensitivity and band. Therefore, the substrate 4 may be a substrate having a low surface roughness.

A first electrode 6 is further formed. The first electrode 6 may be made of a conductive material having a low surface roughness, such as titanium, tungsten, or aluminum. As in the case of the substrate 4, if the first electrode 6 has a high surface roughness, the distance between the first electrode 6 and the second electrode 10 varies among cells or elements because of the surface roughness. Therefore, a conductive material having a low surface roughness may be used. The thickness of the first electrode 6 may be small because the surface roughness increases as the thickness of the first electrode 6 increases.

Next, a second insulating film 7 is formed as illustrated in FIG. 18A. The second insulating film 7 may be made of an insulating material having a low surface roughness. The second insulating film 7 is formed to prevent the electrical short circuit between the first electrode 6 and the second electrode 10 or the dielectric breakdown caused when voltage is applied between the first electrode and the second electrode. The second insulating film 7 is also formed to prevent the first electrode from being etched during removal of a sacrificial layer performed after this process. As in the case of the substrate, if the second insulating film 7 has a high surface roughness, the distance between the first electrode 6 and the second electrode 10 varies among cells because of the surface roughness. Therefore, an insulating film having a low surface roughness may be used. For example, a silicon nitride film or a silicon oxide film is employed. The insulating film has a minimum thickness required to keep insulation because the surface roughness increases as the thickness of the insulating film increases.

Figure 18B:
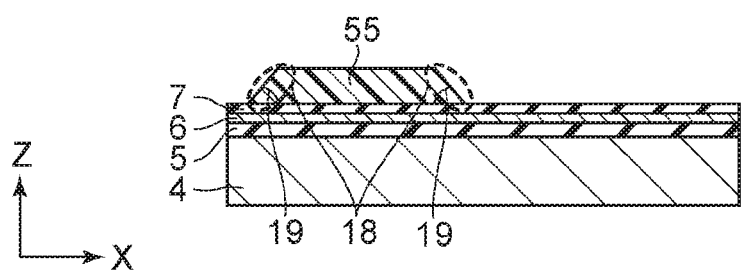
FIG. 18B is a sectional view (a sectional view taken along line A-B in FIG. 1) for describing a method for producing a CMUT according to an embodiment of the present invention.

Next, a sacrificial layer 55 is formed as illustrated in FIG. 18B. Since the outer periphery of the sacrificial layer 55 is to serve as a wall surface of a hollow portion having a tapered shape 18, the sacrificial layer 55 is formed such that the outer periphery of the sacrificial layer 55 has a tapered shape. The sacrificial layer 55 may be made of a material having a low surface roughness. As in the case of the substrate 4, if the sacrificial layer 55 has a high surface roughness, the distance between the first electrode 6 and the second electrode 10 varies among cells because of the surface roughness. Therefore, the sacrificial layer 55 may have a low surface roughness. The sacrificial layer 55 may be made of a material having a high etching rate to shorten the etching time for removing the sacrificial layer 55.

The material for the sacrificial layer and the insulating film need to be combined such that the second insulating film 7 and a third insulating film 9 to serve as a vibration film 12 are substantially not etched with an etchant for removing the sacrificial layer 55. If the second insulating film 7 and a third insulating film 9 to serve as a vibration film 12 are etched with the etchant for removing the sacrificial layer 55, the thickness of the vibration film 12 and the distance between the first electrode 6 and the second electrode 10 vary. The variation in the thickness of the vibration film 12 and the variation in the distance between the first electrode 6 and the second electrode 10 lead to variations in the sensitivity and band among cells.

When the second insulating film 7 and the vibration film 12 are silicon oxide films or silicon nitride films, the sacrificial layer may be made of a material that has a low surface roughness and is etched with an etchant that does not readily etch the second insulating film 7 and the vibration film 12. For example, the combination of the material for the sacrificial layer 55 and the etchant is amorphous silicon and an etching gas containing xenon difluoride. In this combination, the sacrificial layer etching can be performed in a dry process. Therefore, the etching rate of the sacrificial layer is high compared with the sacrificial layer etching in a wet process. Furthermore, sticking specific to the wet process can be avoided.

The tapered shape 18 can be formed by the following method. The material for the sacrificial layer 55 is subjected to film formation, and a resist is formed on a portion in which the sacrificial layer 55 is to be formed. By performing etching in a sacrificial layer pattern while the outer periphery of the resist is caused to recede, the sacrificial layer 55 illustrated in FIG. 18B can be formed. When the resist is formed, a tapered shape may be formed on the periphery of the resist by controlling, for example, the exposure of photolithography, the material for the resist, and the baking temperature.

The taper angle 19 can be controlled by changing parameters such as the types of gases used for patterning the sacrificial layer during etching, the mixing ratio of the gases, the power of plasma, and the degree of vacuum. The types of gases and the mixing ratio of the gases may be appropriately selected in order to obtain a desired taper angle 19. For example, when the material for the sacrificial layer is amorphous silicon, the taper angle 19 can be controlled by changing the flow ratio of $SF_6/O_2$.

Figure 18C:
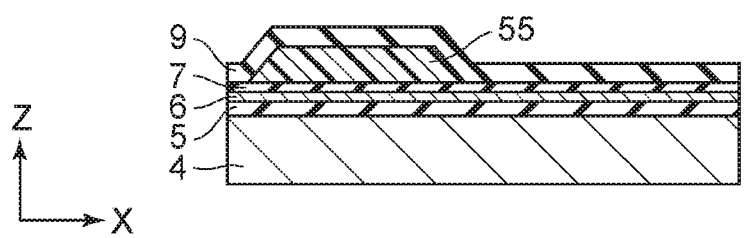
FIG. 18C is a sectional view (a sectional view taken along line A-B in FIG. 1) for describing a method for producing a CMUT according to an embodiment of the present invention.

Next, a third insulating film 9 is formed as illustrated in FIG. 18C. The third insulating film 9 may have a low tensile stress, such as 500 MPa or less. The tensile stress of silicon nitride films can be controlled to a low tensile stress of 500 MPa or less. When a vibration film 12 has compressive stress, the vibration film 12 causes buckling and considerably deforms. In the case of high tensile stress, the third insulating film 9 is sometimes broken. Since silicon nitride films have a higher relative dielectric constant than silicon oxide films, the transmission and reception sensitivity can be improved by decreasing the gap between upper and lower electrodes. Therefore, the third insulating film 9 may be a silicon nitride film. Furthermore, since the third insulating film 9 is formed on the sacrificial layer 55, the third insulating film 9 may have such a thickness that the sacrificial layer 55 can be covered with certainty.

The feature in this embodiment is that the Si/N composition ratio of a silicon nitride film serving as the third insulating film 9 has a distribution in the film. This distribution of the composition ratio may be formed by stacking two or more silicon nitride films having different Si/N composition ratios. Alternatively, the distribution may be formed in a graded manner by changing the film formation parameters such as the flow ratio of raw material gases during film formation by plasma enhanced chemical vapor deposition (PE-CVD). Herein, for the Si/N composition ratio inside the film, the third insulating film 9 has a Si-rich portion at the side in contact with the sacrificial layer 55 and has a N-rich portion toward the second electrode 10 that is not in contact with the sacrificial layer 55.

Figure 18D:
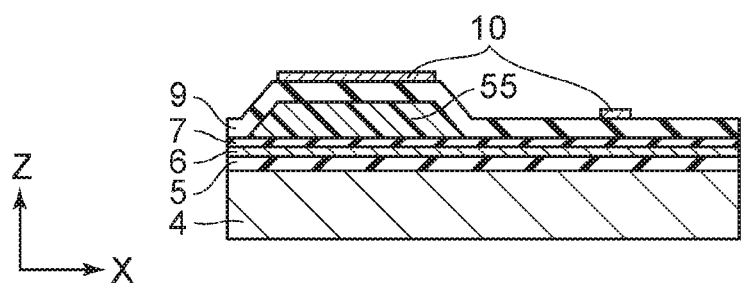
FIG. 18D is a sectional view (a sectional view taken along line A-B in FIG. 1) for describing a method for producing a CMUT according to an embodiment of the present invention.

Next, a second electrode 10 is formed as illustrated in FIG. 18D. The second electrode 10 may be made of a material having a low residual stress, such as aluminum. When a sacrificial layer removing step or a sealing step is performed after formation of the second electrode 10, the second electrode 10 may be made of a material having etching resistance against the sacrificial layer etching and thermal resistance. Such a material is, for example, an aluminum-neodymium alloy or titanium. When the second electrode 10 is formed, the second electrode 10 may have such a thickness that the steps on the surface can be covered with certainty.

Figure 18E:
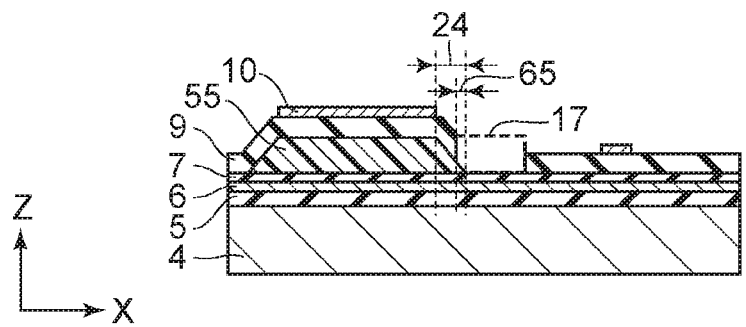
FIG. 18E is a sectional view (a sectional view taken along line A-B in FIG. 1) for describing a method for producing a CMUT according to an embodiment of the present invention.

Next, an etching opening 17 is formed in the third insulating film 9 as illustrated in FIG. 18E. The etching opening 17 is a hole through which an etching gas is introduced to remove the sacrificial layer 55 by etching. As described above, the etching opening 17 may be formed such that the outer periphery of the etching opening 17 partly overlaps a portion in which the wall surface of the hollow portion has a tapered shape 18. Thus, the etching opening 17 can be located near the center of the sacrificial layer 55, which can shorten the time for etching the sacrificial layer 55.

Figure 18F:
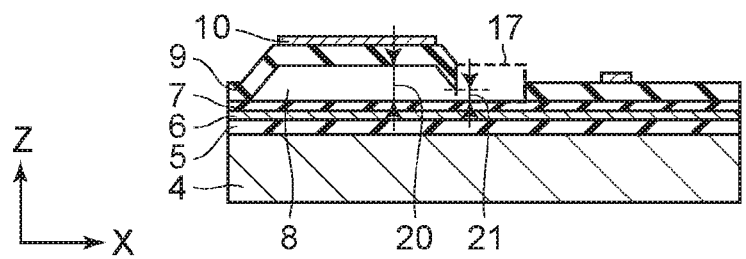
FIG. 18F is a sectional view (a sectional view taken along line A-B in FIG. 1) for describing a method for producing a CMUT according to an embodiment of the present invention.

Next, the sacrificial layer 55 is removed to form a hollow portion 8 as illustrated in FIG. 18F. The sacrificial layer 55 made of amorphous silicon is removed using an etching gas containing xenon difluoride and hydrogen. Alternatively, the sacrificial layer may be removed by a method in Example 1 described later as illustrated in FIG. 19. That is, the second electrode 10 is formed, an insulating film 56 made of the same silicon nitride as the third insulating film 9 is formed on the second electrode 10, and then the etching opening 17 is formed and the sacrificial layer is removed. In the etching gas, for example, $ClF_3$ may be used instead of xenon difluoride.

Figure 18G:
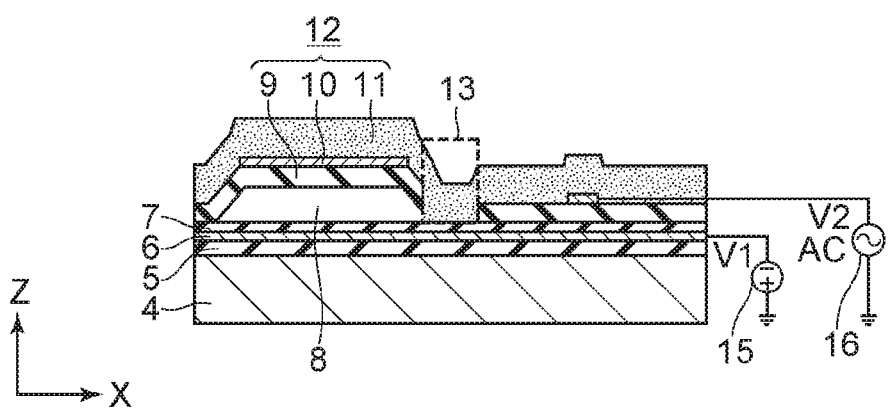
FIG. 18G is a sectional view (a sectional view taken along line A-B in FIG. 1) for describing a method for producing a CMUT according to an embodiment of the present invention.

Next, a sealing film 11 is formed to seal the etching opening 17 as illustrated in FIG. 18G. The third insulating film 9, the second electrode 10, and the sealing film 11 constitute a vibration film 12. The etching opening 17 is sealed with the sealing film 11 to serve as a sealing portion 13. The sealing film 11 needs to prevent liquid and outside air from entering the hollow portion 8. If the pressure of the hollow portion 8 is an atmospheric pressure, the gas inside the hollow portion 8 expands or shrinks as a result of temperature change. Furthermore, since a high electric field is applied to the hollow portion 8, the reliability of elements deteriorates because of ionization of molecules. Therefore, the sealing needs to be performed at a reduced pressure. By reducing the pressure inside the hollow portion 8, the air resistance inside the hollow portion 8 can be decreased. This eases the vibration of the vibration film 12, which can increase the sensitivity of the CMUT 1. As a result of the sealing, the CMUT 1 can be used in a liquid. The sealing material may be the same as that of the third insulating film 9 because of its high adhesiveness. The sealing film 11 may have such a thickness that the steps on the surface can be covered with certainty. When the third insulating film 9 is made of silicon nitride, the sealing film 11 may also be made of silicon nitride.

Through the above steps, the structure illustrated in FIG. 18G is obtained. Thus, the CMUT illustrated in FIG. 1 can be produced. By using a lead-out wire (not illustrated) electrically connected to the second electrode pad 42 in FIG. 2, electric signals can be extracted from the second electrode 10. When the CMUT 1 receives ultrasonic waves, a direct-current voltage is applied to the first electrode 6. When ultrasonic waves are received, the vibration film 12 including the second electrode 10 deforms. Consequently, the height of the hollow portion 8 between the second electrode 10 and the first electrode 6 changes, which changes the capacitance. This change in capacitance allows an electric current to flow through the lead-out wire. The electric current is subjected to current-voltage conversion at the transmission/reception circuit 30 illustrated in FIG. 16, and ultrasonic waves can be received in the form of voltage. When a direct-current voltage is applied to the first electrode 6 and a transmission driving voltage is applied to the second electrode 10, an electrostatic force allows the vibration film 12 to vibrate. Thus, ultrasonic waves can be transmitted.

EXAMPLES

Example 1

In Examples, the structure of a CMUT 1 and the method for producing a CMUT 1 will be described to show the advantageous effects of the present invention. Comparative Examples will also be described. A CMUT 1 in this Example will be described with reference to FIG. 1, FIG. 2, FIG. 18, and FIG. 19. FIG. 19 is a sectional view taken along line A-B in FIG. 1 in which a fourth insulating film 56 is further disposed.

The external dimensions of the CMUT 1 illustrated in FIG. 2 are 12 (mm) in the Y direction and 45 (mm) in the X direction. The external dimensions of each of the elements 3 is 0.3 (mm) in the X direction and 4 (mm) in the Y direction, and 196 elements 3 are arranged in a one-dimensional array. FIG. 18G is a sectional view taken along line A-B in FIG. 1. Each of the cells 2 constituting the elements 3 has a substantially circular shape except for the etching opening 17, and the hollow portion 8 has a diameter of 32 (μm). The diameter of the hollow portion 8 is a diameter of a region of the second insulating film 7 defined by a contact portion between the second insulating film 7 and the third insulating film 9. The cells 2 are arranged in a close-packed manner as illustrated in FIG. 1. In the cells 2 constituting each of the elements 3, the adjacent cells are arranged at a distance of 35 (μm). That is, the minimum distance between hollow portions 8 of the adjacent cells 2 is 3 (μm). All the cells are not illustrated in FIG. 1, but 1013 cells are arranged in each of the elements 3 in reality.

The sectional structure and the production method will be described with reference to FIGS. 18A to 18G. As illustrated in FIGS. 18A to 18G, each of the cells 2 includes a silicon substrate 4 having a thickness of 725 (μm), a first insulating film 5 formed on the silicon substrate 4, a first electrode 6 formed on the first insulating film 5, and a second insulating film 7 on the first electrode 6. The cell 2 further includes a hollow portion 8 and a vibration film 12 including a second electrode 10, a third insulating film 9, and a sealing film 11. The hollow portion 8 has a height of 300 nm. Furthermore, a voltage application unit 15 that applies a bias voltage between the first electrode 6 and the second electrode 10 and a voltage application unit 16 that applies a transmission voltage to the second electrode are provided.

The first insulating film 5 is a thermally oxidized silicon film formed by thermal oxidation and having a thickness of 1 (μm). The second insulating film 7 is a silicon oxide film formed by PE-CVD and having a thickness of 400 nm. The first electrode 6 is made of tungsten and has a thickness of 100 nm. The second electrode 10 is made of an Al—Nd alloy and has a thickness of 100 nm. The third insulating film 9, the fourth insulating film 56, and the sealing film 11 are silicon nitride films formed by PE-CVD so as to have a tensile stress of 450 (MPa) or less. The third insulating film 9 has a thickness of 400 nm and the sealing film 11 has a thickness of 440 nm.

In this Example, film formation is performed to formation of the second insulating film 7 as illustrated in FIG. 18A. Next, an amorphous silicon film serving as a sacrificial layer 55 is formed as illustrated in FIG. 18B. The amorphous silicon film has a thickness of 300 nm. In this Example, the sacrificial layer 55 is formed in such a pattern that the outer periphery of the sacrificial layer 55 has a taper angle 19 of 45°.

Next, a silicon nitride film serving as a third insulating film 9 is formed as illustrated in FIG. 18C. The Si/N composition ratio inside the silicon nitride film has a distribution. The Si/N composition ratio was realized by changing the gas flow ratio of silane ($SiH_4$) and ammonia ($NH_3$) that were raw material gases during formation of the silicon nitride film by PE-CVD. First, a Si-rich silicon nitride film having a thickness of 200 nm was formed directly on the sacrificial layer 55 at an RF power of 480 W at gas flow rates of 50 sccm for $SiH_4$, 40 sccm for $NH_3$, and 625 sccm for nitrogen. The $NH_3/SiH_4$ flow ratio was 0.8 during formation of the Si-rich silicon nitride film. Subsequently, a N-rich silicon nitride film having a thickness of 200 nm was formed at an RF power of 275 W at gas flow rates of 20 sccm for $SiH_4$, 200 sccm for $NH_3$, and 600 sccm for nitrogen. The $NH_3/SiH_4$ gas flow ratio was 10 during formation of the N-rich silicon nitride film, which showed that the $NH_3$ flow rate was higher than that during formation of the Si-rich silicon nitride film.

As described above, for the Si/N composition ratio inside the film, the silicon nitride film had a Si-rich portion at the side in contact with the sacrificial layer 55 and had a N-rich portion toward the second electrode 10 not in contact with the sacrificial layer 55. The third insulating film 9 having such a distribution of the Si/N composition ratio was formed so as to have a thickness of 400 nm. The term "Si-rich" or "N-rich" in this Example refers to a difference in the relative composition ratio inside the third insulating film 9, and does not mean that $Si_3N_4$ that is a stoichiometric composition is Si-rich or N-rich.

To evaluate the compositions of the N-rich silicon nitride film and the Si-rich silicon nitride film, the refractive index was measured by ellipsometry and the infrared absorption spectrum (FT-IR) was measured. The refractive index is known to have a very high correlation with the Si/N composition ratio of the film. The refractive index increases as the Si/N composition ratio increases, that is, the film becomes more Si-rich. The Si—H/N—H bond area ratio can be calculated from the infrared absorption spectrum using a N—H stretching mode near 3350 $cm^{-1}$ and a Si—H stretching mode near 2160 $cm^{-1}$ of the silicon nitride film. The above-described Si-rich silicon nitride film used in this Example had a refractive index of 2.0 and a Si—H/N—H bond area ratio of 1.1. On the other hand, the N-rich silicon nitride film had a refractive index of 1.86 and a Si—H/N—H bond area ratio of 0.05. The imbalance of the Si or N content can be evaluated from the refractive index and the infrared absorption spectrum.

Next, film formation is performed to formation of the second electrode 10 as illustrated in FIG. 18D. The second electrode 10 is made of an aluminum-neodymium alloy and has a thickness of 100 nm.

Next, an etching opening 17 is formed as illustrated in FIG. 18E. In this Example, one etching opening 17 is formed for each of the cells 2. The etching opening 17 has a semicircular shape with an overlapping width 26 of 9.0 (μm) as illustrated in FIG. 1. The etching opening 17 is formed at such a position that the overlapping distance 65 between the etching opening 17 and the outer periphery of the sacrificial layer 55 is 100 nm.

Next, the sacrificial layer 55 is removed to form a hollow portion 8 as illustrated in FIG. 18F. The sacrificial layer 55 made of amorphous silicon is removed by performing dry etching using, as an etching gas, a mixed gas containing xenon difluoride and hydrogen. Herein, the device used for the sacrificial layer etching is Sentry SVR-XeF2 manufactured by Memsstar. First, a sample was set to a sample stage of the etching device. Then, the sacrificial layer was etched under the following etching conditions to form a hollow portion 8: chamber pressure 9.5 Torr, carrier nitrogen flow rate 50 sccm, xenon difluoride flow rate 20 sccm, hydrogen flow rate 20 sccm, substrate temperature 15° C., and etching time 15 minutes. A problem did not occur in which, during the sacrificial layer etching, deposits were generated on the surface of the third insulating film 9 and blocked the hollow portion to inhibit the etching as observed in Comparative Example 1 described later.

Next, a sealing film 11 having a thickness of 440 nm is formed as illustrated in FIG. 18G. The sealing film 11 is a silicon nitride film formed by PE-CVD. Finally, the back surface of the silicon substrate 4 was subjected to backgrinding to decrease the substrate thickness from 750 μm to 300 μm.

The thus-obtained CMUT 1 in Example 1 had desired vibration characteristics. The electrostatic voltage after a voltage of 200 V was applied was reduced to 0.01 V and the electrostatic voltage after a pull-in voltage of 260 V was applied was reduced to 0.2 V, which were the amounts of electrostatic charge tolerable for practical use. The same effects were produced even when the thickness of the Si-rich film was changed, instead of 200 nm, from a small thickness of 20 nm to 200 nm while the total thickness of the third insulating film 9 was maintained at 400 nm.

In this Example, the structure in which the vibration film 12 is constituted by the third insulating film 9, the second electrode 10, and the sealing film 11 has been described. The same results are obtained even when a fourth insulating film 56 is disposed between the second electrode 10 and the sealing film 11 as illustrated in FIG. 19. When the fourth insulating film 56 is disposed, it suffices that a fourth insulating film 56 is formed after formation of the second electrode 10 in FIG. 18D, and then the steps in FIGS. 18E to 18G are performed.

In the structure illustrated in FIG. 19, the films are typically as follows. The first insulating film 5 is a thermally oxidized silicon film formed by thermal oxidation and having a thickness of 1 (μm). The second insulating film 7 is a silicon oxide film formed by PE-CVD and having a thickness of 400 nm. The first electrode 6 is made of tungsten and having a thickness of 100 nm. The second electrode 10 is made of an Al—Nd alloy and having a thickness of 100 nm. The third insulating film 9, the fourth insulating film 56, and the sealing film 11 are silicon nitride films formed by PE-CVD so as to have a tensile stress of 450 (MPa) or less. The third insulating film has a distribution of the Si/N composition ratio therein, which is constituted by a Si-rich silicon nitride film formed at the side in contact with the sacrificial layer 55 so as to have a thickness of 200 nm and a N-rich silicon nitride film formed toward the second electrode 10 that is not in contact with the sacrificial layer 55 so as to have a thickness of 400 nm. Thus, a third insulating film 9 having a thickness of 600 nm is formed. The fourth insulating film 56 has a thickness of 450 nm and the sealing film 11 has a thickness of 1050 nm. The height of the hollow portion 8 is 350 nm, and the thickness of the amorphous silicon film serving as the sacrificial layer 55 corresponding to the hollow portion 8 is also 350 nm.

Comparative Example 1

Next, an example in which a single N-rich silicon nitride film having no distribution of the Si/N composition ratio therein is used as the third insulating film 9 unlike in Example 1 will be described. Comparative Example 1 is the same as Example 1, except that a single N-rich silicon nitride film having a thickness of 400 nm is used as the third insulating film 9.

In this configuration, the sacrificial layer was etched under the following conditions: chamber pressure 9.5 Torr, carrier nitrogen flow rate 50 sccm, xenon difluoride flow rate 20 sccm, hydrogen flow rate 20 sccm, substrate temperature 15° C., and etching time 15 minutes. However, unlike in Example 1, the sacrificial layer etching was delayed and the sacrificial layer was not completely removed within 15 minutes of the etching time. Even if the etching time was extended, the progress of etching was slow, resulting in etching failure.

As a result of the observation of a hollow portion section of the etching failure sample with a scanning electron microscope, it was found that granular deposits were grown on the surface of the third insulating film on the hollow portion side to block the hollow portion serving as a channel of the etching gas. That is, the etching was delayed because the hollow portion narrowed down as the deposits grew during etching of the sacrificial layer, which decreased the amount of the etching gas that reached the sacrificial layer.

In the CMUT 1 in Comparative Example 1, the hollow portion could not be formed because of etching failure and thus desired vibration characteristics were not achieved.

Comparative Example 2

Next, an example in which a single Si-rich silicon nitride film having no distribution of the Si/N composition ratio therein is used as the third insulating film 9 unlike in Example 1 will be described. Comparative Example 2 is the same as Example 1, except that a Si-rich silicon nitride film having a thickness of 400 nm is used as the third insulating film 9.

In this configuration, the sacrificial layer was etched under the following conditions: chamber pressure 9.5 Torr, carrier nitrogen flow rate 50 sccm, xenon difluoride flow rate 20 sccm, hydrogen flow rate 20 sccm, substrate temperature 15° C., and etching time 15 minutes. A problem did not occur in which, during the sacrificial layer etching, deposits were generated on the surface of the third insulating film 9 and blocked the hollow portion to inhibit the etching as observed in Comparative Example 1.

In the thus-obtained CMUT 1 in Comparative Example 2, the hollow portion was formed, but a problem occurred in terms of electrostatic characteristics. The electrostatic voltage after a voltage of 200 V was applied was 21 V and the electrostatic voltage after a pull-in voltage of 260 V was applied was 52 V, which were the amounts of electrostatic charge intolerable for practical use.

A charge trap is present in the silicon nitride film. It is generally known that the charge trap density is dependent on the Si/N composition ratio of the silicon nitride film, and the charge trap density tends to increase as the film becomes more Si-rich. In Comparative Example 2, the third insulating film 9 in contact with the second electrode 10 is a Si-rich silicon nitride film, and thus charges are easily accumulated in the charge trap during voltage application. Therefore, the amount of electrostatic charge of the CMUT was large after voltage application and thus electrostatic charge could not be suppressed.

When only a Si-rich silicon nitride film is used as the third insulating film 9 as in Comparative Example 2, etching failure, such as delay or stop of etching, does not readily occur during etching of a sacrificial layer with an etching gas containing xenon difluoride and hydrogen. However, the electrostatic characteristics of the CMUT deteriorate because of low nitrogen content.

Example 2

In Example 2, a method for producing a hollow structure in which the sacrificial layer is made of silicon and at least one of upper and lower films that sandwich the sacrificial layer is a silicon nitride film will be described. In Example 2, first, a structure for evaluating the characteristics of a silicon nitride film, which is illustrated in a schematic sectional view of FIG. 22, was used. The growth rate of deposits on the silicon nitride film during the sacrificial layer etching with an etching gas containing xenon difluoride and hydrogen, which is not described in Example 1, Comparative Example 1, and Comparative Example 2, was measured. In addition, the thickness decrease rate of the silicon nitride film itself, that is, the etching rate was measured by providing levels having different Si/N composition ratios.

As illustrated in the sectional view before etching in FIG. 22, silicon nitride films with levels having different Si/N composition ratios were formed as a membrane 43 on a silicon substrate serving as the supporting substrate 4 so as to have a total thickness of 1 μm. Then, a rectangular opening having a width of 100 μm and a length of 5 mm was formed as the etching opening 17 through which an etching gas can enter the membrane 43. In this case, silicon of the silicon substrate serves as a material for the sacrificial layer, and a portion formed by etching the silicon serves as the hollow portion 8. For the silicon nitride films with levels having different Si/N composition ratios, the refractive index was determined by ellipsometry and the Si—H/N—H bond area ratio was determined from the infrared absorption spectrum before etching.

Subsequently, the sacrificial layer was etched for 30 minutes using, as an etching gas, a gas containing the xenon difluoride and hydrogen having the same flow ratio as in Example 1 and carrier nitrogen. As illustrated in the sectional view after etching in FIG. 22, the silicon was isotropically etched centering on the opening 17, and the thickness of the silicon nitride film 43 thereon was also slightly decreased. In addition, a deposit 44 grew on the surface of the silicon nitride film. The decrease in the thickness of the silicon nitride film and the thickness of the deposit were observed with a scanning electron microscope.

Table 1 collectively shows the results. The film formation conditions of the silicon nitride film of the level 1 are those of the Si-rich silicon nitride film in Example 1. The silicon nitride film of the level 3 is a N-rich silicon nitride film. The silicon nitride film of the level 2 is formed at gas flow rates of 160 sccm for SiH$_4$, 127 sccm for NH$_3$, and 2000 sccm for nitrogen at an RF power of 980 W. The film of the level 4 is a multilayer film obtained by forming a Si-rich silicon nitride film that is the same as that of the level 1 and has a thickness of 300 nm, a N-rich silicon nitride film that is the same as that of the level 3 and has a thickness of 400 nm, and a Si-rich silicon nitride film that is the same as that of the level 1 and has a thickness of 300 nm on a silicon substrate in this order. In the level 4, the face exposed to the etching gas is a Si-rich silicon nitride film. Since the film of the level 4 is a multilayer body of silicon nitride films, the refractive index and the Si—H/N—H bond area ratio are omitted in Table 1.

TABLE 1

| Name of sample | Refractive index (633 nm) | Si—H/N—H bond area ratio | Etching rate of silicon nitride film (nm/min) | Deposit growth rate (nm/min) |
|---|---|---|---|---|
| Level 1 | 2.00 | 1.1 | 1.4 | 1.5 |
| Level 2 | 1.90 | 0.6 | 1.6 | 1.4 |
| Level 3 | 1.86 | 0.05 | 2.1 | 6.8 |
| Level 4 | — | — | 2.3 | 2.1 |

As is clear from the results in Table 1, the silicon nitride films of the level 1 (refractive index 2.00) and the level 2 (refractive index 1.90) have deposit growth rates equal to the etching rates of the silicon nitride films. In contrast, the silicon nitride film of the level 3 (refractive index 1.86) has a deposit growth rate much higher than the etching rate of the silicon nitride film. This means that the thickness of the silicon nitride film itself is decreased during etching, but the total thickness of the silicon nitride film and the deposit layer is increased. That is, when a silicon nitride film having a deposit growth rate higher than the etching rate of the silicon nitride film is used as a membrane during formation of the hollow structure, the progress of sacrificial layer etching facilitates the blocking of the hollow portion as shown in Comparative Example 1. This poses a problem in that the etching rate of the sacrificial layer etching decreases or the sacrificial layer etching stops.

As a result of the analysis from the infrared absorption spectrum, the resulting deposit is assumed to be ammonium fluorosilicate. It has been confirmed that the deposit grows only on the surface of the silicon nitride film and does not grow when an etching gas containing xenon difluoride and carrier nitrogen without hydrogen is used. From these results, ammonium fluorosilicate is assumed to grow using a nitrogen atom on the surface of the silicon nitride film as a raw material. That is, a N-rich silicon nitride containing a larger amount of nitrogen atom serving as a raw material for the deposit probably has a higher deposit growth rate. Note that ammonium fluorosilicate that sublimates under heating at about 200° C. at reduced pressure can be removed in the subsequent step.

As is clear from the results of the level 4, even when the silicon nitride film of the level 3 having a high deposit growth rate is used, the growth of the deposit can be suppressed by covering the surface of the silicon nitride film exposed to the etching gas with the silicon nitride film of the level 1.

As described above, when a hollow structure is produced by etching the sacrificial layer using an etching gas containing xenon difluoride and hydrogen, the Si/N composition ratio of the silicon nitride film is important. The silicon nitride film that can suppress blocking of the hollow portion due to the deposit during sacrificial layer etching is a silicon nitride film that satisfies the requirement that the deposit growth rate is lower than the etching rate of the silicon nitride film during formation of a desired hollow structure. For this requirement, it has been found in Examples that the hollow portion is not easily blocked when a silicon nitride film having a refractive index of 1.90 or more, which is referred to as a Si-rich silicon nitride film, is used.

FIG. 23 is a schematic sectional view before and after the sacrificial layer etching in the production of the hollow structure. A silicon nitride film having a thickness of 400 nm was formed as a first film 45 on a silicon substrate serving as the supporting substrate 4, and an amorphous silicon film having a thickness of 300 nm was formed thereon as the sacrificial layer 55. Furthermore, a silicon nitride film having a thickness of 400 nm was formed as a second film 46, and a rectangular opening having a width of 100 μm and a length of 5 mm was formed as an etching opening 17 through which an etching gas can enter the second film 46. The sacrificial layer was etched for 30 minutes using, as an etching gas, a gas containing the xenon difluoride and hydrogen having the same flow ratio as in Example 1 and carrier nitrogen. After the sacrificial layer etching, the sacrificial layer 55 changes into a hollow portion 8.

When the Si-rich silicon nitride film of the level 1 or the level 2 was used as the first film 45 and the second film 46, blocking of the hollow portion due to the deposit during the sacrificial layer etching was not observed and the etching smoothly proceeded, and thus the hollow structure could be obtained. In contrast, when the N-rich silicon nitride film of the level 3 was used, the deposit considerably grew and the tendency to block the hollow portion was observed, which posed a problem of delay of the sacrificial layer etching.

Herein, for both the first film 45 and the second film 46, the Si-rich silicon nitride film (200 nm) of the level 1 was provided on the side in contact with the sacrificial layer 55, and the N-rich silicon nitride film (200 nm) of the level 3 was provided on the side not in contact with the sacrificial layer 55. In this case, only the Si-rich silicon nitride film was exposed to the etching gas. As a result of this covering effect, etching smoothly proceeded and the hollow structure could be obtained. When the N-rich silicon nitride film that causes blocking is used, the etching characteristics can be improved by forming a composition ratio distribution inside the N-rich silicon nitride film having a surface on which a Si-rich silicon nitride film is disposed. Herein, the structure in which a silicon nitride film having a Si/N composition ratio distribution is used for both the first film 45 and the second film 46 has been described. However, at least one of the first film 45 and the second film 46 may be a silicon nitride film having a Si/N composition ratio distribution, and the other may be formed of, for example, a metal, a dielectric, or a resin having high etching selectivity that is substantially not etched even if being exposed to an etching gas. For example, a metal such as aluminum, nickel, chromium, or platinum is suitable because such a metal is not easily etched by xenon difluoride. A dielectric such as lead zirconate titanate (PZT), zinc oxide, or aluminum nitride can be used as a piezoelectric material for piezoelectric elements. A resin such as a typical photoresist or polydimethylsiloxane (PDMS) can also be used.

In the multilayer structure in FIG. 23, the Si-rich silicon nitride film (200 nm) and the N-rich silicon nitride film (200 nm) of the level 3 that is not in contact with the sacrificial layer have the same thickness, but the thicknesses are not necessarily the same. This is because the advantageous effects of Examples are produced by using a Si-rich silicon nitride film having a deposit growth rate lower than the etching rate of the silicon nitride film during the sacrificial layer etching.

Therefore, it suffices that the Si-rich silicon nitride film has a thickness larger than or equal to the minimum thickness at which the Si-rich silicon nitride film is not eliminated for a desired etching time of the sacrificial layer such that the N-rich silicon nitride film is not exposed. For example, when the Si-rich silicon nitride film of the level 1 is used, a thickness of 42 nm is decreased for an etching time of 30 minutes. Therefore, the thickness of the Si-rich silicon nitride film can be set to 42 nm or more and the N-rich silicon nitride film has a residual thickness of 358 nm. Moreover, even when the thickness of the Si-rich silicon nitride film is smaller than the minimum thickness, the exposure of the N-rich silicon nitride film can be prevented for an etching time corresponding to the thickness of the Si-rich silicon nitride film. As a result, blocking of the hollow portion due to the deposit can be suppressed.

The hollow structure according to this embodiment can be used for pressure sensors, ultrasonic sensors, tactile sensors, and infrared sensors (heat insulation structure for bolometer).

The method for producing a hollow structure according to an embodiment of the present invention can overcome etching failure by controlling the composition ratio of nitrogen and silicon in a silicon nitride film to suppress the growth of deposits during etching.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A hollow structure comprising:
   a first film; and
   a second film disposed so as to face the first film with a hollow portion formed therebetween,
   wherein at least one of the first film and the second film includes a silicon nitride film, and
   in the silicon nitride film, a composition ratio of silicon to nitrogen in a first region having a face in contact with the hollow portion is larger than a composition ratio of silicon to nitrogen in a second region not including the first region.

2. The hollow structure according to claim 1, wherein the silicon nitride film has a refractive index of 1.90 or more at a wavelength of 633 nm.

3. A capacitive transducer comprising:
   a first electrode;
   a first film disposed on the first electrode;
   a second film disposed so as to face the first film with a hollow portion formed therebetween; and
   a second electrode disposed on the second film,
   wherein at least one of the first film and the second film includes a silicon nitride film, and
   in the silicon nitride film, a composition ratio of silicon to nitrogen in a first region having a face in contact with the hollow portion is larger than a composition ratio of silicon to nitrogen in a second region not including the first region.

4. The capacitive transducer according to claim 3, wherein the silicon nitride film has a refractive index of 1.90 or more at a wavelength of 633 nm.

5. The hollow structure according to claim 1, wherein one of the first film and the second film includes a silicon nitride film and the other includes a silicon oxide film.

6. The hollow structure according to claim 1, wherein the silicon nitride film has a structure in which a ratio of silicon to nitrogen continuously decreases from one main surface at which the silicon nitride film is in contact with the sacrificial layer toward the other main surface.

7. The hollow structure according to claim 1, wherein the first region has a thickness of 42 nm or more in a direction in which the silicon nitride film is formed.

8. The hollow structure according to claim 1, wherein in the silicon nitride film, a composition ratio of silicon to nitrogen in a third region having a face opposite to the face in contact with the sacrificial layer is larger than a composition ratio of silicon to nitrogen in the second region.

9. The capacitive transducer according to claim 3, wherein one of the first film and the second film includes a silicon nitride film and the other includes a silicon oxide film.

10. The capacitive transducer according to claim 3, wherein the silicon nitride film has a structure in which a ratio of silicon to nitrogen continuously decreases from one main surface at which the silicon nitride film is in contact with the sacrificial layer toward the other main surface.

11. The capacitive transducer according to claim 3, wherein the first region has a thickness of 42 nm or more in a direction in which the silicon nitride film is formed.

12. The capacitive transducer according to claim 3, wherein in the silicon nitride film, a composition ratio of silicon to nitrogen in a third region having a face opposite to the face in contact with the sacrificial layer is larger than a composition ratio of silicon to nitrogen in the second region.

* * * * *